(12) United States Patent
Galley et al.

(10) Patent No.: US 9,487,501 B2
(45) Date of Patent: Nov. 8, 2016

(54) PYRAZOLE CARBOXAMIDE COMPOUNDS AND USES THEREOF

(71) Applicant: Hoffmann-La Roche Inc., Little Falls, NJ (US)

(72) Inventors: Guido Galley, Rheinfelden (DE); Roger Norcross, Olsberg (CH); Philippe Pflieger, Schwoben (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 60 days.

(21) Appl. No.: 14/656,853

(22) Filed: Mar. 13, 2015

(65) Prior Publication Data

US 2015/0218131 A1 Aug. 6, 2015

Related U.S. Application Data

(63) Continuation of application No. PCT/EP2013/068769, filed on Sep. 11, 2013.

(30) Foreign Application Priority Data

Sep. 14, 2012 (EP) ..................... 12184360

(51) Int. Cl.
C07D 401/12 (2006.01)
C07D 403/12 (2006.01)
C07D 413/12 (2006.01)
C07D 413/14 (2006.01)
C07D 417/14 (2006.01)

(52) U.S. Cl.
CPC ............ C07D 401/12 (2013.01); C07D 403/12 (2013.01); C07D 413/12 (2013.01); C07D 413/14 (2013.01); C07D 417/14 (2013.01)

(58) Field of Classification Search
CPC C07D 401/12; C07D 403/12; C07D 413/12; C07D 417/14
See application file for complete search history.

(56) References Cited

U.S. PATENT DOCUMENTS

2011/0152245 A1 6/2011 Groebke Zbinden et al.

FOREIGN PATENT DOCUMENTS

| CL | 3484-13 | 12/2012 |
|---|---|---|
| TW | 201130828 | 9/2011 |
| WO | 2011/076678 | 6/2011 |
| WO | 2012/063896 | 5/2012 |
| WO | 2012/168260 | 12/2012 |

OTHER PUBLICATIONS

International Search Report and Written Opinion on patentability for International Patent Application No. PCT/EP2013/068769, Oct. 2013.

*Primary Examiner* — Rebecca Anderson

(57) ABSTRACT

The present invention relates to compounds of formula

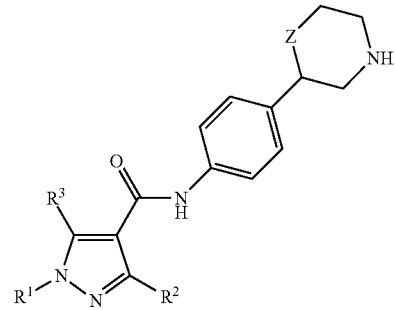

I wherein $R^1$, $R^2$, $R^3$, and Z are as descried in the claims, or to a pharmaceutically suitable acid addition salt thereof. It has not been found that the compounds of formula I has a good affinity to the trace amine associated receptors (TAARs), especially for TAAR1. The compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

15 Claims, No Drawings

PYRAZOLE CARBOXAMIDE COMPOUNDS AND USES THEREOF

CROSS REFERENCE TO RELATED APPLICATIONS

This application is a continuation application and claims priority under 35 U.S.C. 365(c) to International Application No. PCT/EP2013/068769, filed on Sep. 11, 2013, which claims priority EP Application No. 12184360.1 filed on Sep. 14, 2012. The entire content of the applications referenced above are hereby incorporated by reference herein.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression[7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors. Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF INVENTION

In one aspect, the present invention relates to compounds of formula

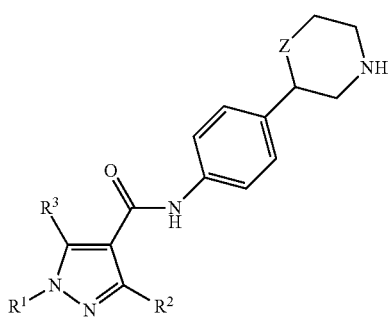

wherein
$R^1$ is phenyl, optionally substituted by halogen, lower alkyl, lower cycloalkyl, lower alkoxy, cyano, lower alkyl substituted by halogen, lower alkyl substituted by hydroxy, lower alkoxy substituted by halogen or lower alkoxy substituted by hydroxy; or is pyridine-2, 3 or 4-yl, optionally substituted by halogen, lower alkyl, lower cycloalkyl, cyano, lower alkyl substituted by halogen, lower alkyl substituted by hydroxy, lower alkoxy, lower alkoxy substituted by halogen or lower alkoxy substituted by hydroxyl; or is pyrimidin-2, 4 or 5-yl, optionally substituted by halogen, lower alkyl, lower cycloalkyl, lower alkyl substituted by hydroxy or lower alkyl substituted by halogen; or is pyrazin-2-yl, optionally substituted by halogen, lower alkyl, lower cycloalkyl, lower alkyl substituted by halogen, lower alkyl substituted by hydroxy or cyano; or is 2,2-difluorobenzo[d][1,3]dioxol-5-yl, or is thiazolyl, optionally substituted by lower alkyl substituted by halogen;
$R^2$ is hydrogen or lower alkyl;
$R^3$ is hydrogen, amino or lower alkyl;
Z is a bond, —$CH_2$— or —O—;
or to a pharmaceutically suitable acid addition salt thereof.

The invention includes all racemic mixtures, all their corresponding enantiomers and/or optical isomers. In addition, all tautomeric forms of compounds of formula I are also encompassed by the present invention.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

It has now been found that the compounds of formula I have a good affinity to the trace amine associated receptors (TAARs), especially for TAAR1.

In one embodiment, the compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In another embodiment, objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD) and diabetes.

DEFINITIONS

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower cycloalkyl" denotes a saturated carbon ring, containing from 3 to 6 carbon atoms, for example cyclopropyl, cyclobutyl, cyclopentyl or cyclohexyl.

As used herein, the term "lower alkyl substituted by halogen" denotes a lower alkyl group as defined above, wherein at least one hydrogen atom is replaced by halogen.

As used herein, the term "lower alkyl substituted by hydroxy" denotes a lower alkyl group as defined above, wherein at least one hydrogen atom is replaced by hydroxy.

As used herein, the term "lower alkoxy" denotes a group wherein the alkyl residue is as defined above and which is attached via an oxygen atom.

The term "halogen" denotes chlorine, iodine, fluorine and bromine.

As used herein, the term "lower alkoxy substituted by halogen" denotes an alkoxy group as defined above and wherein at least one hydrogen atom is replaced by halogen.

As used herein, the term "lower alkoxy substituted by hydroxy" denotes an alkoxy group as defined above and wherein at least one hydrogen atom is replaced by hydroxy.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

One embodiment of the invention are compounds of formula IA

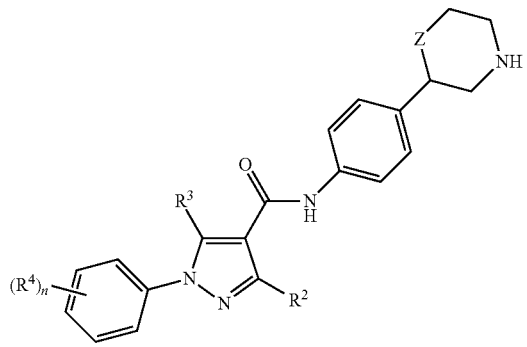

wherein
R² is hydrogen or lower alkyl;
R³ is hydrogen, amino or lower alkyl;
R⁴ is hydrogen, halogen, lower alkyl, lower cycloalkyl, lower alkoxy, cyano, lower alkyl substituted by halogen, lower alkyl substituted by hydroxyl, lower alkoxy substituted by halogen or lower alkoxy substituted by hydroxy;
n is 1 or 2;
Z is a bond, —CH₂— or —O—;
or a pharmaceutically suitable acid addition salt thereof, for example the compounds
(S)-5-methyl-N-(4-(morpholin-2-yl)phenyl)-1-phenyl-1H-pyrazole-4-carboxamide
(S)-5-amino-1-(4-fluorophenyl)-N-(4-(morpholin-2-yl)phenyl)-1H-pyrazole-4-carboxamide
(S)-1-(4-methoxyphenyl)-N-(4-(morpholin-2-yl)phenyl)-1H-pyrazole-4-carboxamide
(S)-1-(4-fluorophenyl)-N-(4-(morpholin-2-yl)phenyl)-1H-pyrazole-4-carboxamide
(S)-1-(3-fluorophenyl)-N-(4-(morpholin-2-yl)phenyl)-1H-pyrazole-4-carboxamide
(S)-1-(4-cyanophenyl)-N-(4-(morpholin-2-yl)phenyl)-1H-pyrazole-4-carboxamide
(R)-1-(4-fluorophenyl)-N-(4-(morpholin-2-yl)phenyl)-1H-pyrazole-4-carboxamide
(S)-1-(3-cyanophenyl)-N-(4-(morpholin-2-yl)phenyl)-1H-pyrazole-4-carboxamide
(S)-1-(4-bromo-2-cyanophenyl)-N-(4-(morpholin-2-yl)phenyl)-1H-pyrazole-4-carboxamide
(S)-1-(4-(difluoromethoxy)phenyl)-N-(4-(morpholin-2-yl)phenyl)-1H-pyrazole-4-carboxamide
(S)-1-(3-(difluoromethoxy)phenyl)-N-(4-(morpholin-2-yl)phenyl)-1H-pyrazole-4-carboxamide
(S)-1-(4-cyano-2-fluorophenyl)-N-(4-(morpholin-2-yl)phenyl)-1H-pyrazole-4-carboxamide
(S)-1-(4-cyano-3-fluorophenyl)-N-(4-(morpholin-2-yl)phenyl)-1H-pyrazole-4-carboxamide
(S)-1-(2-cyano-4-fluorophenyl)-N-(4-(morpholin-2-yl)phenyl)-1H-pyrazole-4-carboxamide
(S)—N-(4-(morpholin-2-yl)phenyl)-1-(4-(trifluoromethoxy)phenyl)-1H-pyrazole-4-carboxamide
(R)-1-(4-(difluoromethoxy)phenyl)-N-(4-(morpholin-2-yl)phenyl)-1H-pyrazole-4-carboxamide
(S)-1-(4-(difluoromethoxy)phenyl)-5-methyl-N-(4-(morpholin-2-yl)phenyl)-1H-pyrazole-4-carboxamide
(S)-1-(4-(difluoromethoxy)phenyl)-3-methyl-N-(4-(morpholin-2-yl)phenyl)-1H-pyrazole-4-carboxamide
(S)-1-(4-cyanophenyl)-5-methyl-N-(4-(morpholin-2-yl)phenyl)-1H-pyrazole-4-carboxamide
(R)-1-(4-cyano-2-fluorophenyl)-N-(4-(morpholin-2-yl)phenyl)-1H-pyrazole-4-carboxamide
(RS)-1-(4-difluoromethoxy-phenyl)-1H-pyrazole-4-carboxylic acid (4-pyrrolidin-3-yl-phenyl)-amide or
(RS)-1-(4-difluoromethoxy-phenyl)-1H-pyrazole-4-carboxylic acid (4-piperidin-3-yl-phenyl)-amide.

One further embodiment of the invention are compounds of formula IB

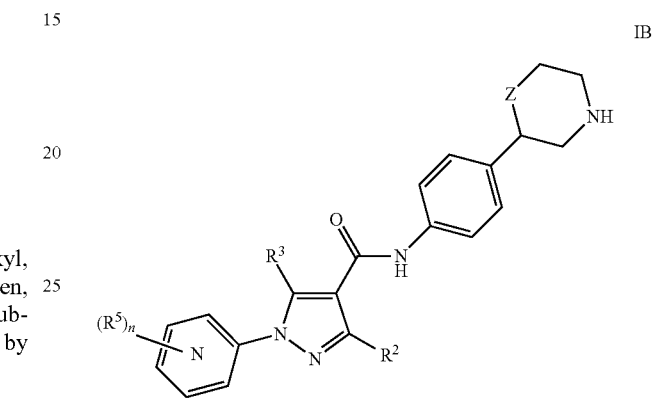

wherein

is pyridine-2, 3 or 4-yl;
R² is hydrogen or lower alkyl;
R³ is hydrogen, amino or lower alkyl;
R⁵ is hydrogen, halogen, lower alkyl, lower cycloalkyl, cyano, lower alkyl substituted by halogen, lower alkyl substituted by hydroxy, lower alkoxy, lower alkoxy substituted by halogen, lower alkoxy substituted by hydroxy;
n is 1 or 2;
Z is a bond, —CH₂— or —O—;
or a pharmaceutically suitable acid addition salt thereof, for example the compounds
(S)-1-(5-chloropyridin-2-yl)-N-(4-(morpholin-2-yl)phenyl)-1H-pyrazole-4-carboxamide
(S)-1-(5-cyanopyridin-2-yl)-N-(4-(morpholin-2-yl)phenyl)-1H-pyrazole-4-carboxamide
(S)-1-(5-bromopyridin-2-yl)-N-(4-(morpholin-2-yl)phenyl)-1H-pyrazole-4-carboxamide
(S)-1-(5-iodopyridin-2-yl)-N-(4-(morpholin-2-yl)phenyl)-1H-pyrazole-4-carboxamide
(S)—N-(4-(morpholin-2-yl)phenyl)-1-(5-(trifluoromethyl)pyridin-2-yl)-1H-pyrazole-4-carboxamide
(S)—N-(4-(morpholin-2-yl)phenyl)-1-(4-(trifluoromethyl)pyridin-2-yl)-1H-pyrazole-4-carboxamide
(S)-1-(4-chloropyridin-2-yl)-N-(4-(morpholin-2-yl)phenyl)-1H-pyrazole-4-carboxamide
(S)-1-(2-bromopyridin-4-yl)-N-(4-(morpholin-2-yl)phenyl)-1H-pyrazole-4-carboxamide
(S)-1-(6-methoxypyridin-2-yl)-N-(4-(morpholin-2-yl)phenyl)-1H-pyrazole-4-carboxamide (S)-1-(3-fluoro-5-(trifluoromethyl)pyridin-2-yl)-N-(4-(morpholin-2-yl)phenyl)-1H-pyrazole-4-carboxamide
(S)-1-(2-chloropyridin-4-yl)-N-(4-(morpholin-2-yl)phenyl)-1H-pyrazole-4-carboxamide
(S)-1-(6-ethoxypyridin-2-yl)-N-(4-(morpholin-2-yl)phenyl)-1H-pyrazole-4-carboxamide
(S)—N-(4-(morpholin-2-yl)phenyl)-1-(2-(trifluoromethyl)pyridin-4-yl)-1H-pyrazole-4-carboxamide or
(S)—N-(4-(morpholin-2-yl)phenyl)-1-(6-(trifluoromethyl)pyridin-3-yl)-1H-pyrazole-4-carboxamide.

One further embodiment of the invention are compounds of formulas IC1, IC2 and IC3

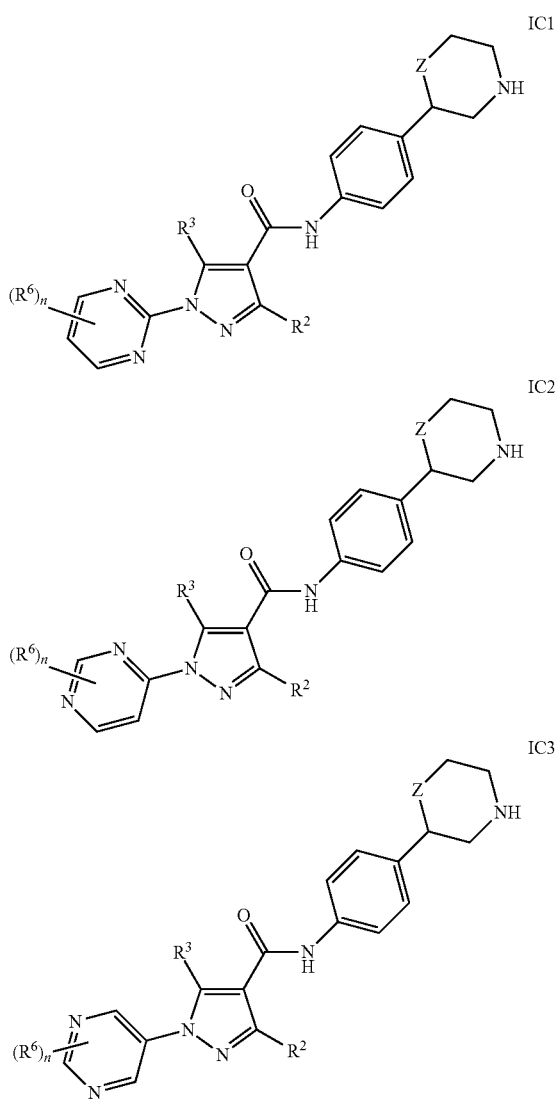

wherein
R² is hydrogen or lower alkyl;
R³ is hydrogen, amino or lower alkyl;
R⁶ is hydrogen, halogen, lower alkyl, lower cycloalkyl, lower alkyl substituted by halogen, or lower alkyl substituted by hydroxy;
Z is a bond, —CH₂— or —O—;
or a pharmaceutically suitable acid addition salt thereof, for example the following compounds (S)-1-(5-chloropyrimidin-2-yl)-N-(4-(morpholin-2-yl)phenyl)-1H-pyrazole-4-carboxamide
(S)—N-(4-(morpholin-2-yl)phenyl)-1-(2-(trifluoromethyl)pyrimidin-4-yl)-1H-pyrazole-4-carboxamide
(S)-1-(2-chloropyrimidin-4-yl)-N-(4-(morpholin-2-yl)phenyl)-1H-pyrazole-4-carboxamide
(S)—N-(4-(morpholin-2-yl)phenyl)-1-(5-(trifluoromethyl)pyrimidin-2-yl)-1H-pyrazole-4-carboxamide
(S)-1-(4-methylpyrimidin-2-yl)-N-(4-(morpholin-2-yl)phenyl)-1H-pyrazole-4-carboxamide
(S)—N-(4-(morpholin-2-yl)phenyl)-1-(6-(trifluoromethyl)pyrimidin-4-yl)-1H-pyrazole-4-carboxamide
(S)—N-(4-(morpholin-2-yl)phenyl)-1-(2-(trifluoromethyl)pyrimidin-5-yl)-1H-pyrazole-4-carboxamide
(S)—N-(4-(morpholin-2-yl)phenyl)-1-(4-(trifluoromethyl)pyrimidin-2-yl)-1H-pyrazole-4-carboxamide or
(S)-1-(6-cyclopropylpyrimidin-4-yl)-N-(4-(morpholin-2-yl)phenyl)-1H-pyrazole-4-carboxamide.

One further embodiment of the invention are compounds of formulas ID

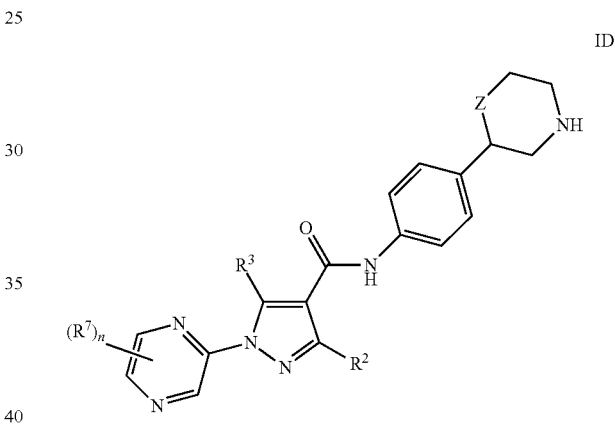

wherein
R² is hydrogen or lower alkyl;
R³ is hydrogen, amino or lower alkyl;
R⁷ is hydrogen, halogen, lower alkyl, lower cycloalkyl, lower alkyl substituted by halogen, lower alkyl substituted by hydroxyl or cyano;
Z is a bond, —CH₂— or —O—;
or a pharmaceutically suitable acid addition salt thereof, for example the following compounds
(S)—N-(4-(morpholin-2-yl)phenyl)-1-(6-(trifluoromethyl)pyrazin-2-yl)-1H-pyrazole-4-carboxamide
(S)-1-(6-methylpyrazin-2-yl)-N-(4-(morpholin-2-yl)phenyl)-1H-pyrazole-4-carboxamide
(S)-1-(5-methylpyrazin-2-yl)-N-(4-(morpholin-2-yl)phenyl)-1H-pyrazole-4-carboxamide
(S)-1-(3-chloropyrazin-2-yl)-N-(4-(morpholin-2-yl)phenyl)-1H-pyrazole-4-carboxamide
(S)-1-(5-cyanopyrazin-2-yl)-N-(4-(morpholin-2-yl)phenyl)-1H-pyrazole-4-carboxamide
(S)-1-(5-chloropyrazin-2-yl)-N-(4-(morpholin-2-yl)phenyl)-1H-pyrazole-4-carboxamide
(S)-1-(6-cyanopyrazin-2-yl)-N-(4-(morpholin-2-yl)phenyl)-1H-pyrazole-4-carboxamide (S)-1-(3-cyanopyrazin-2-yl)-N-(4-(morpholin-2-yl)phenyl)-1H-pyrazole-4-carboxamide or
(S)—N-(4-(morpholin-2-yl)phenyl)-1-(5-(trifluoromethyl)pyrazin-2-yl)-1H-pyrazole-4-carboxamide.

One further embodiment of the invention are compounds of formulas IE

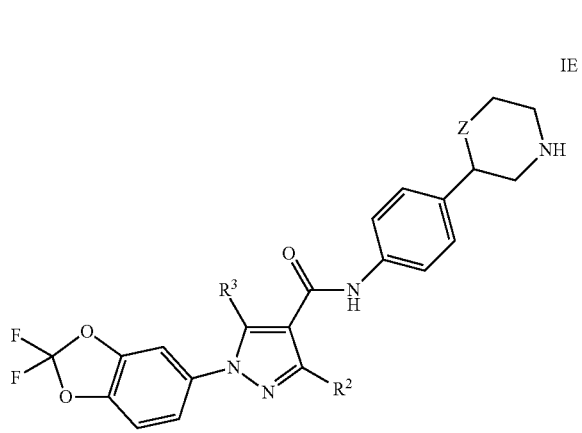

IE wherein
R² is hydrogen or lower alkyl;
R³ is hydrogen, amino or lower alkyl
Z is a bond, —CH₂— or —O—;
or a pharmaceutically suitable acid addition salt thereof, for example the following compound (S)-1-(2,2-difluorobenzo[d][1,3]dioxol-5-yl)-N-(4-(morpholin-2-yl)phenyl)-1H-pyrazole-4-carboxamide.

One further embodiment of the invention are compounds of formulas IF

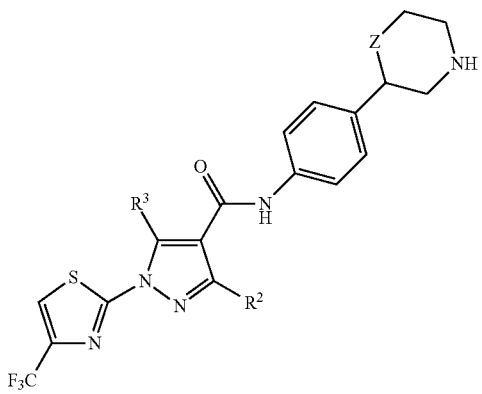

IF wherein
R² is hydrogen or lower alkyl;
R³ is hydrogen, amino or lower alkyl
Z is a bond, —CH₂— or —O—;
or a pharmaceutically suitable acid addition salt thereof, for example the following compound (S)—N-(4-(morpholin-2-yl)phenyl)-1-(4-(trifluoromethyl)thiazol-2-yl)-1H-pyrazole-4-carboxamide.

The present compounds of formula I and their pharmaceutically acceptable salts can be prepared by methods known in the art, for example, by processes described below, which process comprises cleaving off the protecting group of compounds of formula

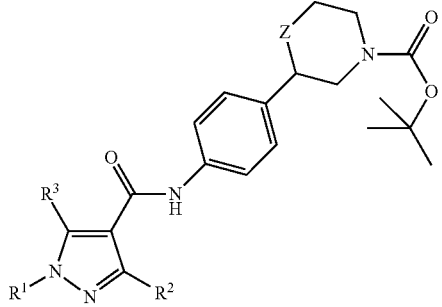

4 to form a compound of formula I

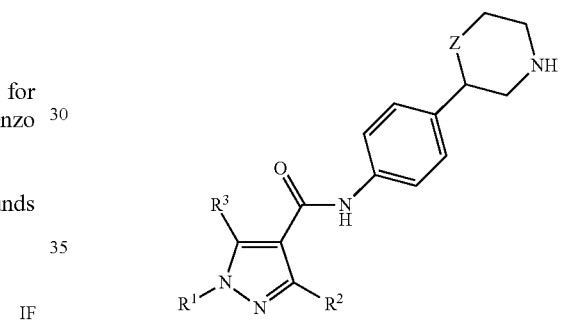

I and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1 and in the description of 55 specific examples. The skills required for carrying out the reactions and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

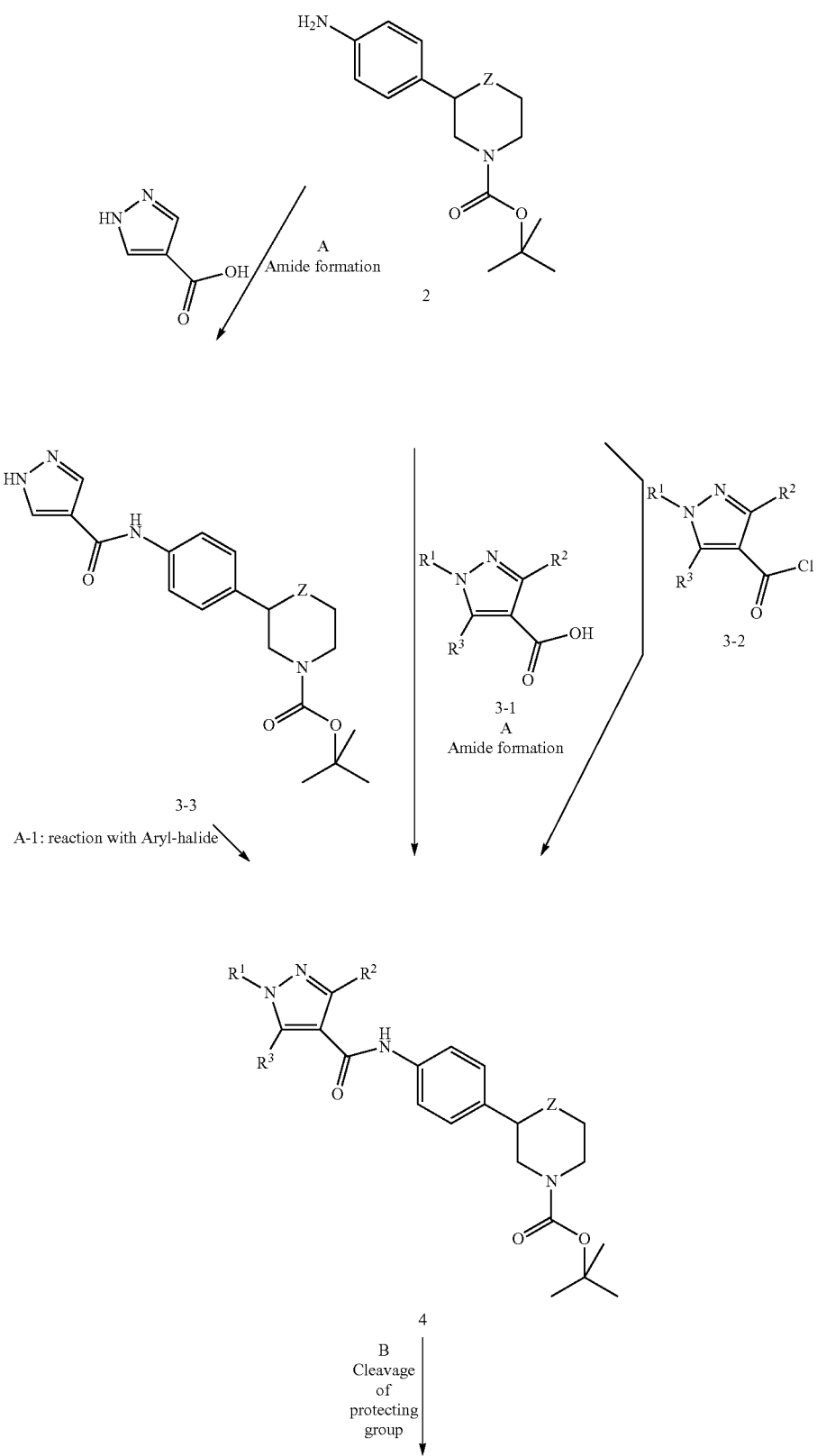

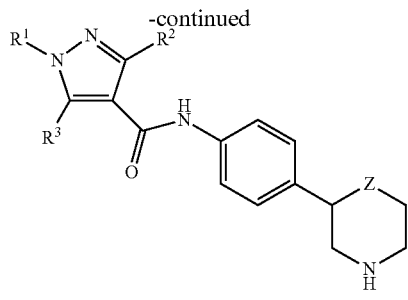

I

For example using:

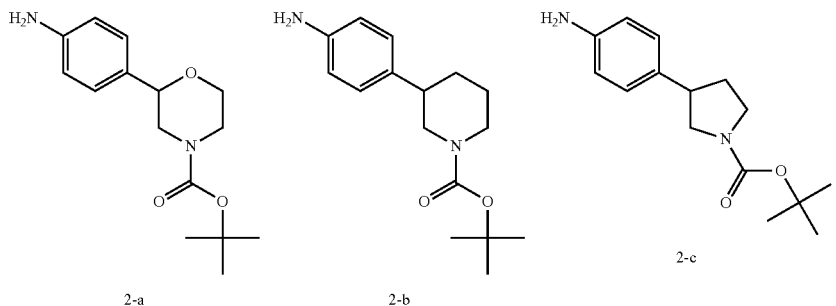

2-a  2-b  2-c wherein $R^1$, $R^2$, $R^3$ and Z are as described above.

Step A:

Amide formation can be accomplished by a coupling reaction between an amine 2 and acid chloride compounds 3-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Examples of appropriate amines 2 include N-protected morpholine derivatives such as 2-a [CAS 1002726-96-6], piperidine derivatives such as 2-b [CAS 875798-79-1], pyrrolidine derivatives such as 2-c [CAS 908334-28-1]. Preferred conditions are triethylamine in THF at room temperature for 18 hours.

If desired, the acyl chloride compound 3-2 may be prepared in situ from the corresponding carboxylic acid 3-1 by treatment with oxalyl chloride or 1-chloro-N,N-2-trimethypropenylamine in halogenated solvents such as dichloromethane or 1,2-dichloroethane or ethereal solvents such as diethyl ether, dioxane, THF, DME or TBME in the presence of a catalyst such as DMF. Preferred conditions are dichloromethane at room temperature for 1 hour.

Alternatively, amide formation can be accomplished by a coupling reaction between an amine 2 and carboxylic acids 3-1 in the presence of a coupling reagent such as DCC, EDC, TBTU, HBTU or HATU in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME. Preferred conditions are BTU with N-methylmorpholine in DMF at 60° C. for 18 hours.

Step A-1:

Reaction of pyrazole intermediate 3-3 with aryl-halides in a solvent such as DMSO or DMF at 0 to 150° C. Preferred conditions are DMSO at 120° C. for 1-20 h.

Step B:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, Dioxane, MeOH, EtOH or $H_2O$ at 0 to 80° C. Preferred conditions are HCl in dioxane at 60° C. for 1-20 h.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

EXAMPLES

Example 1

(S)-5-methyl-N-(4-(morpholin-2-yl)phenyl)-1-phenyl-1H-pyrazole-4-carboxamide hydrochloride

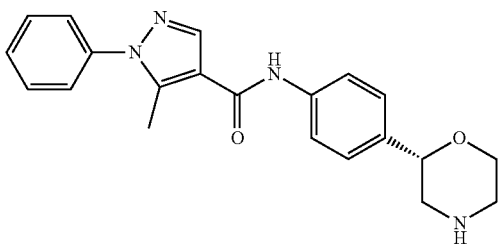 [SMILES: Cc1c(C(=O)Nc2ccc([C@H]3CNCCO3)cc2)cnn1-c1ccccc1]

a) Preparation of (S)-tert-butyl 2-(4-(5-methyl-1-phenyl-1H-pyrazole-4-carboxamido)phenyl)morpholine-4-carboxylate (S)-tert-butyl 2-(4-aminophenyl)morpholine-4-carboxylate (40 mg, 144 µmol, Eq: 1.00), 5-methyl-1-phenyl-1H-pyrazole-4-carboxylic acid (CAS 91138-00-0) (37.8 mg, 187 µmol, Eq: 1.3) and HBTU (81.8 mg, 216 µmol, Eq: 1.5) were dissolved in THF (2.00 ml), treated with N-methylmorpholine (43.6 mg, 47.4 µl, 431 µmol, Eq: 3) and stirred at room temperature for 17 hours. The reaction mixture was poured into water (10 ml) and extracted twice with EtOAc. The organic layers were washed with brine, dried over MgSO$_4$, filtered and concentrated in vacuo. The crude material was purified by column chromatography (8 g silica gel, eluent: heptane/EtOAc 2:1) to give the title compound as a white solid (120 mg, 74.5%). MS (ISP): 407.4 ([M+H]$^+$-tBu).

b) Preparation of (S)-5-methyl-N-(4-(morpholin-2-yl)phenyl)-1-phenyl-1H-pyrazole-4-carboxamide hydrochloride (S)-tert-butyl 2-(4-(5-methyl-1-phenyl-1H-pyrazole-4-carboxamido)phenyl)morpholine-4-carboxylate (18.4 mg, 39.8 µmol, Eq: 1.00) were dissolved in tetrahydrofuran (0.75 ml) and treated with 4 M HCl in dioxane (149 µl, 597 µmol, Eq: 15). The reaction mixture was stirred at 60° C. for 5 hours, cooled to room temperature, filtered off and dried under high vacuum to give the target compound as an off-white solid (14.6 mg, 92%). MS (ISP): 363.5 ([M+H]$^+$).

Preparation of (S)-tert-butyl 2-(4-aminophenyl)morpholine-4-carboxylate

Step a) (S)-2-(4-bromophenyl)morpholine 2.27 g (RS)-2-(4-bromo-phenyl)-morpholine (CAS-1131220-82-0) were separated on a Chiralpak IA (8×32 cm) HPLC column using n-heptane/ethanol (1:11)+0.1% DEA.
(S)-2-(4-bromo-phenyl)-morpholine: fractions collected from 7.6 min to 9.4 min.
Yield 0.97 g (42.9%) with 97.4% ee
(R)-2-(4-bromo-phenyl)-morpholine: fractions collected from 9.8 min to 13.9 min
Yield 0.99 g (43.6%) with 97.4% ee Step b) (S)-tert-butyl 2-(4-bromophenyl)morpholine-4-carboxylate (S)-2-(4-bromo-phenyl)-morpholine (36.3 g, 150 mmol) and N,N-diisopropylethylamine (23.3 g, 31.4 ml, 180 mmol) in THF (360 ml) were treated with di-tert-butyl dicarbonate (39.3 g, 180 mmol). The reaction mixture was stirred for 17 h at rt, concentrated in vacuo, diluted with ethyl acetate, washed with 1 M citric acid (2×100 ml), dried over magnesium sulfate, filtered and concentrated in vacuo. The crude material was crystallized from hexane to afford 47.1 g (92%) (S)-tert-butyl 2-(4-bromophenyl)morpholine-4-carboxylate as an off-white solid. MS (ISP): 344.1 ([M+H]$^+$).

Step c) (S)-tert-butyl 2-(4-(diphenylmethyleneamino)phenyl)morpholine-4-carboxylate (S)-tert-butyl 2-(4-bromophenyl)morpholine-4-carboxylate (47 g, 137 mmol), diphenylmethanimine (29.9 g, 27.6 m, 165 mmol), BINAP (6.41 g, 10.3 mmol) and Pd$_2$(dba)$_3$ (3.14 g, 3.43 mmol) were dissolved under Argon in dry and de-aerated toluene (940 ml) and treated with sodium tert-butoxide (18.5 g, 192 mmol). The dark brown mixture was stirred at 90° C. for 18 h. The yellow/brown reaction mixture was diluted with toluene (700 ml), cooled to rt and extracted twice with water. The organic layer was separated, dried over magnesium sulfate and concentrated in vacuo. The crude product was diluted with 300 ml hexane, stirred for 1 h and filtered off, leading to an orange solid (68 g) which was purified by column chromatography (1.3 kg silicagel, 20% ethylacetate/heptane). The combined and concentrated fractions were suspended in hexane, stirred for 17 h, filtered off and dried under high vacuum, to yield 54.1 g (89%) yellow solid. MS (ISP): 443.3 ([M+H]$^+$).

Step d) (S)-tert-butyl 2-(4-aminophenyl)morpholine-4-carboxylate

A suspension of (S)-tert-butyl 2-(4-(diphenylmethyleneamino)phenyl)morpholine-4-carboxylate (54.1 g, 122 mmol), ammonium formate (116 g, 1.83 mol) and 5% Pd/C (6.5 g, 3.06 mmol) in methanol (930 ml) was stirred at 60° C. for 2 h. The reaction mixture was filtered and concentrated in vacuo. The residue was dissolved in ethyl acetate and water. The organic phase was extracted twice with 0.5 M HCl. The combined aqueous phases were basified with 2 M NaOH and extracted twice with DCM. The organic phases were dried over magnesium sulfate, filtered and dried in vacuo, to yield 31.95 g off-white solid. MS (ISP): 279.1 ([M+H]$^+$).

Example 2

(S)-5-amino-1-(4-fluorophenyl)-N-(4-(morpholin-2-yl)phenyl)-1H-pyrazole-4-carboxamide dihydrochloride

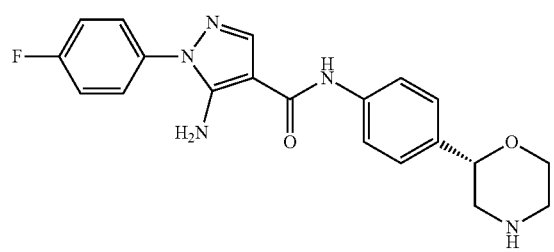 [SMILES: Nc1c(C(=O)Nc2ccc([C@H]3CNCCO3)cc2)cnn1-c1ccc(F)cc1]

The title compound was prepared in analogy to Example 1 using 5-amino-1-(4-fluoro-phenyl)-1H-pyrazole-4-carboxylic acid (CAS 187949-90-2) instead of 5-methyl-1-phenyl-1H-pyrazole-4-carboxylic acid.

Light brown solid. MS (ISP): 382.2 ([M+H]$^+$).

Example 3

(S)-1-(4-methoxyphenyl)-N-(4-(morpholin-2-yl) phenyl)-1H-pyrazole-4-carboxamide hydrochloride

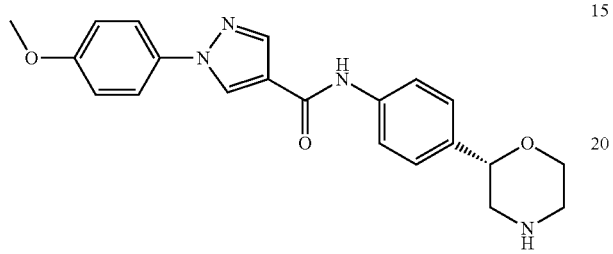

The title compound was prepared in analogy to Example 1 using 1-(4-methoxy-phenyl)-1H-pyrazole-4-carboxylic acid (CAS 138907-79-6) instead of 5-methyl-1-phenyl-1H-pyrazole-4-carboxylic acid.

Light brown solid. MS (ISP): 379.4 ([M+H]$^+$).

Example 4

(S)-1-(4-fluorophenyl)-N-(4-(morpholin-2-yl)phenyl)-1H-pyrazole-4-carboxamide hydrochloride

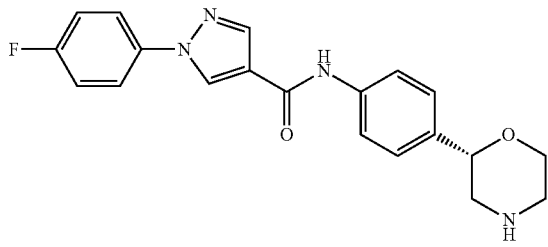 [SMILES: O=C(Nc1ccc([C@H]2CNCCO2)cc1)c1cnn(-c2ccc(F)cc2)c1]

a) (S)-tert-butyl 2-(4-(1-(4-fluorophenyl)-1H-pyrazole-4-carboxamido)phenyl)morpholine-4-carboxylate To a solution of (S)-tert-butyl 2-(4-aminophenyl)morpholine-4-carboxylate (50 mg, 180 µmol, Eq: 1.00), 1-(4-fluorophenyl)-1H-pyrazole-4-carboxylic acid (CAS 138907-81-0) (37.0 mg, 180 µmol, Eq: 1.00) and HBTU (102 mg, 269 µmol, Eq: 1.5) in DMF (4 ml) was added N-methylmorpholine (54.5 mg, 59.2 µl, 539 µmol, Eq: 3). The reaction mixture was stirred for 2 days at room temperature. The reaction mixture was poured in 20 ml water, extracted twice with EtOAc, washed with brine, and the organic layer was dried over MgSO$_4$ and evaporated in vacuo. The crude material was purified by flash chromatography (Silicycle Si-column 20 g, 20% to 25% EtOAc in heptane) leading to a white solid (43 mg, 51%). MS (ISP): 467.2 ([M+H]$^+$).

b) (S)-1-(4-fluorophenyl)-N-(4-(morpholin-2-yl) phenyl)-1H-pyrazole-4-carboxamide hydrochloride To a suspension of (S)-tert-butyl 2-(4-(1-(4-fluorophenyl)-1H-pyrazole-4-carboxamido)phenyl)morpholine-4-carboxylate (43 mg, 92.2 µmol, Eq: 1.00) in dioxane (200 µl) was added 4 M HCl in dioxane (346 µl, 1.38 mmol, Eq: 15). The reaction suspension was stirred at 60° C. for 2 hours. The suspension was cooled down, diluted with 3 ml dioxane, filtered off, washed with ether and dried under high vacuum.

White solid. MS: 367.1 ([M+H]$^+$).

Example 5

(S)-1-(3-fluorophenyl)-N-(4-(morpholin-2-yl)phenyl)-1H-pyrazole-4-carboxamide hydrochloride

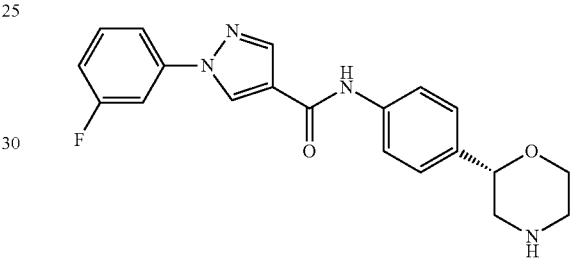

The title compound was prepared in analogy to Example 4 using 1-(3-fluoro-phenyl)-1H-pyrazole-4-carboxylic acid instead of 1-(4-fluorophenyl)-1H-pyrazole-4-carboxylic acid and by heating at 60° C. for 17 hours instead room temperature in step a).

Off-white solid. MS (ISP): 367.1 ([M+H]$^+$).

Preparation of 1-(3-fluorophenyl)-1H-pyrazole-4-carboxylic acid

A solution of ethyl 5-amino-1-(3-fluorophenyl)-1H-pyrazole-4-carboxylate (CAS 138907-70-7) (1.596 g, 6.4 mmol, Eq: 1.00) and isopentyl nitrite (1.13 g, 1.28 ml, 9.61 mmol, Eq: 1.5) in THF (41.6 ml) was refluxed for 3 h. The reaction was not complete after 3 h. 0.2 Equivalent more of isopentyl nitrite was added to the mixture and stirred at reflux overnight. The solution was concentrated in vacuo to give a solid. To this solid was added heptane and the yellow suspension was filtered to give a light-yellow solid which was dissolved in THF (20 ml) and MeOH (4.00 ml) and treated with 1 M LiOH (9.65 ml, 9.65 mmol, Eq: 2). The mixture was stirred overnight. After addition of LiOH the solution became brown. To the residue was added water and 1 N HCl (pH:1), this aqueous phase was extracted two times with ethyl acetate, the resulting organic layers were combined and washed with brine, then dried over MgSO$_4$, filtered and concentrated in vacuo to give 1-(3-fluorophenyl)-1H-pyrazole-4-carboxylic acid (880 mg, 88%) as a light-brown solid. MS: 205.0 ([M−H]$^-$).

Example 6

(S)-1-(4-cyanophenyl)-N-(4-(morpholin-2-yl)phenyl)-1H-pyrazole-4-carboxamide hydrochloride

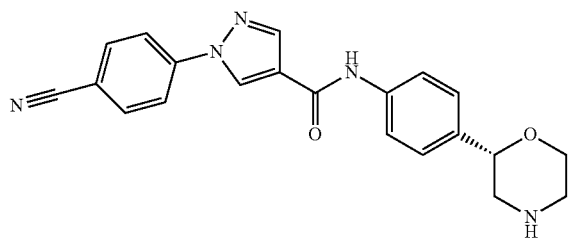 [SMILES: N#Cc1ccc(-n2cc(C(=O)Nc3ccc([C@H]4CNCCO4)cc3)cn2)cc1]

The title compound was prepared in analogy to Example 5 using 1-(4-cyano-phenyl)-1H-pyrazole-4-carboxylic acid (CAS 1152945-21-5) instead of 1-(3-fluorophenyl)-1H-pyrazole-4-carboxylic acid in step a).
White solid. MS (ISP): 374.2 ([M+H]$^+$).

Example 7

(S)-1-(5-chloropyridin-2-yl)-N-(4-(morpholin-2-yl)phenyl)-1H-pyrazole-4-carboxamide hydrochloride

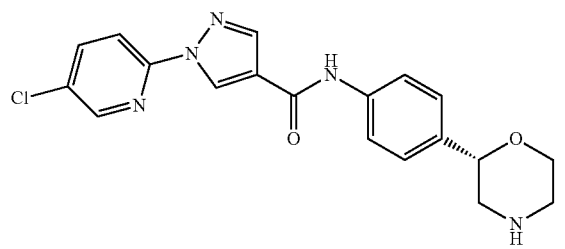 [SMILES: O=C(Nc1ccc([C@H]2CNCCO2)cc1)c1cnn(-c2ccc(Cl)cn2)c1]

The title compound was prepared in analogy to Example 5 using 1-(5-chloro-pyridin-2-yl)-1H-pyrazole-4-carboxylic acid (CAS 1247865-00-4) instead of 1-(3-fluorophenyl)-1H-pyrazole-4-carboxylic acid in step a).
Light yellow solid. MS (ISP): 384.2 ([M+H]$^+$).

Example 8

(S)-1-(5-cyanopyridin-2-yl)-N-(4-(morpholin-2-yl)phenyl)-1H-pyrazole-4-carboxamide hydrochloride

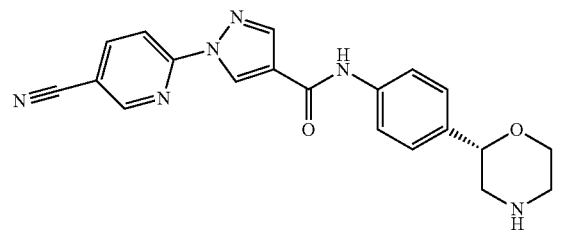

The title compound was prepared in analogy to Example 5 using 1-(5-cyano-pyridin-2-yl)-1H-pyrazole-4-carboxylic acid (CAS 1248081-54-0) instead of 1-(3-fluorophenyl)-1H-pyrazole-4-carboxylic acid in step a).
Light yellow solid. MS (ISP): 375.3 ([M+H]$^+$).

Example 9

(S)-1-(5-bromopyridin-2-yl)-N-(4-(morpholin-2-yl)phenyl)-1H-pyrazole-4-carboxamide hydrochloride

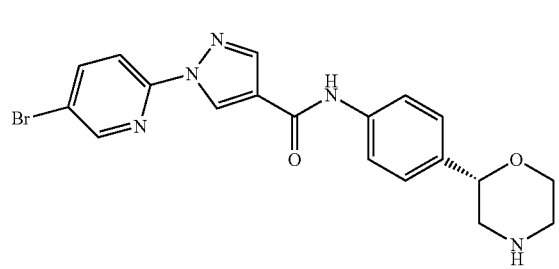

The title compound was prepared in analogy to Example 5 using 1-(5-bromo-pyridin-2-yl)-1H-pyrazole-4-carboxylic acid (CAS 1249288-99-0) instead of 1-(3-fluorophenyl)-1H-pyrazole-4-carboxylic acid in step a).
Light yellow solid. MS (ISP): 430.1 ([M+H]$^+$).

Example 10

(S)-1-(5-iodopyridin-2-yl)-N-(4-(morpholin-2-yl)phenyl)-1H-pyrazole-4-carboxamide hydrochloride

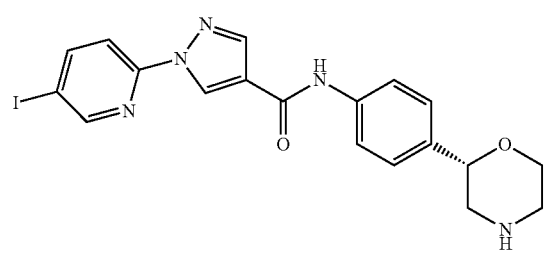 [SMILES: O=C(Nc1ccc([C@H]2CNCCO2)cc1)c1cnn(-c2ccc(I)cn2)c1]

The title compound was prepared in analogy to Example 5 using 1-(5-iodo-pyridin-2-yl)-1H-pyrazole-4-carboxylic acid (CAS 1373148-07-2) instead of 1-(3-fluorophenyl)-1H-pyrazole-4-carboxylic acid in step a).
Off-white solid. MS (ISP): 476.1 ([M+H]$^+$).

Example 11

(S)—N-(4-(morpholin-2-yl)phenyl)-1-(5-(trifluoromethyl)pyridin-2-yl)-1H-pyrazole-4-carboxamide hydrochloride

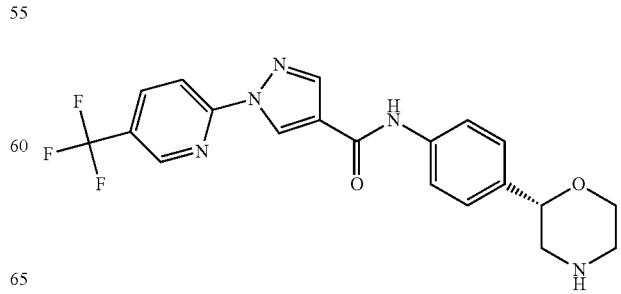

The title compound was prepared in analogy to Example 5 using 1-(5-trifluoromethyl-pyridin-2-yl)-1H-pyrazole-4-carboxylic acid (CAS 1006465-65-1) instead of 1-(3-fluorophenyl)-1H-pyrazole-4-carboxylic acid in step a).

Light yellow solid. MS (ISP): 418.2 ([M+H]⁺).

Example 12

(R)-1-(4-fluorophenyl)-N-(4-(morpholin-2-yl)phenyl)-1H-pyrazole-4-carboxamide hydrochloride

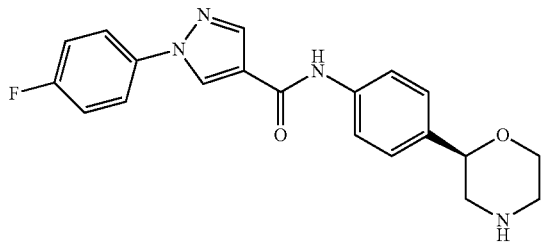 [SMILES: O=C(Nc1ccc([C@@H]2CNCCO2)cc1)c1cnn(-c2ccc(F)cc2)c1]

The title compound was prepared in analogy to Example 4, step a) using (R)-tert-butyl 2-(4-aminophenyl)morpholine-4-carboxylate instead of (S)-tert-butyl 2-(4-aminophenyl)morpholine-4-carboxylate and reacting at 60° C. for 4 h instead of 2 days at room temperature in step a).

White solid. MS (ISP): 367.1 ([M+H]⁺).

Preparation of (R)-tert-butyl 2-(4-aminophenyl)morpholine-4-carboxylate

Step a) (R)-2-(4-bromophenyl)morpholine 2.27 g (RS)-2-(4-bromo-phenyl)-morpholine (CAS-1131220-82-0) were separated on a Chiralpak IA (8×32 cm) HPLC column using n-heptane/ethanol (1:11)+0.1% DEA.
(S)-2-(4-bromo-phenyl)-morpholine: fractions collected from 7.6 min to 9.4 min.
Yield 0.97 g (42.9%) with 97.4% ee
(R)-2-(4-bromo-phenyl)-morpholine: fractions collected from 9.8 min to 13.9 min
Yield 0.99 g (43.6%) with 97.4% ee Step b) (R)-tert-butyl 2-(4-bromophenyl)morpholine-4-carboxylate (R)-2-(4-Bromophenyl)morpholine (6 g, 24.8 mmol) and N,N-diisopropylethylamine (3.84 g, 5.19 ml, 29.7 mmol) in THF (60 ml) were treated with di-tert-butyl dicarbonate (6.49 g, 29.7 mmol). The reaction mixture was stirred for 17 h at rt, concentrated in vacuo, diluted with ethyl acetate, washed with 1 M citric acid, dried over magnesium sulfate, filtered and concentrated in vacuo. The crude material was crystallized from heptane/ethyl acetate to afford 8.48 g (87%) (R)-tert-butyl 2-(4-bromophenyl)morpholine-4-carboxylate as a white solid. MS (ISP): 344.1 ([M+H]⁺).

Step c) (R)-tert-butyl 2-(4-(diphenylmethyleneamino)phenyl)morpholine-4-carboxylate (R)-tert-butyl 2-(4-bromophenyl)morpholine-4-carboxylate (5.4 g, 15.8 mmol), diphenylmethanimine (3.43 g, 3.17 ml, 18.9 mmol), BINAP (737 mg, 1.18 mmol) and Pd₂(dba)₃ (361 mg, 0.39 mmol) were dissolved under argon in dry and de-aerated toluene (108 ml) and treated with sodium tert-butoxide (2.12 g, 22.1 mmol). The dark brown mixture was stirred at 90° C. for 18 h. The yellow/brown reaction mixture was diluted with toluene (100 ml), cooled to rt and extracted twice with water. The organic layer was separated, dried over magnesium sulfate and concentrated in vacuo. The crude product was diluted with 50 ml hexane, stirred for 1 h and filtered off, leading to a yellow solid (7.4 g) which was purified by column chromatography (50 g silicagel, 5% to 15% ethylacetate/heptane). The combined and concentrated fractions were suspended in hexane, stirred for 17 h, filtered off andf dried under high vacuum, to yield 6.15 g (86%) yellow solid. MS (ISP): 443.4 ([M+H]⁺).

Step d) (R)-tert-butyl 2-(4-aminophenyl)morpholine-4-carboxylate

A suspension of (R)-tert-butyl 2-(4-(diphenylmethyleneamino)phenyl)morpholine-4-carboxylate (6 g, 13.6 mmol), ammonium formate (12.8 g, 203 mmol) and 5% Pd/C (721 mg, 0.339 mmol) in methanol (103 ml) was stirred at 60° C. for 2 h. The reaction mixture was filtered and concentrated. The residue was dissolved in ethyl acetate and water. The organic phase was extracted twice with 0.5 M HCl. The combined aqueous phases were basified with 2 M NaOH and extracted twice with DCM. The organic phases were dried over magnesium sulfate, filtered and dried in vacuo, to yield 3.04 g off-white solid. MS (ISP): 279.1 ([M+H]⁺).

Example 13

(S)-1-(3-cyanophenyl)-N-(4-(morpholin-2-yl)phenyl)-1H-pyrazole-4-carboxamide hydrochloride

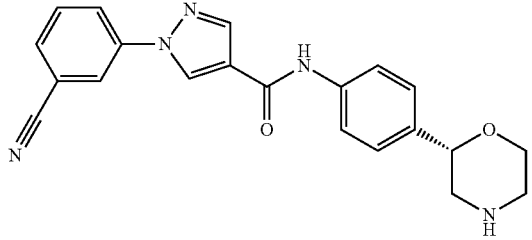 [SMILES: N#Cc1cccc(-n2cc(C(=O)Nc3ccc([C@H]4CNCCO4)cc3)cn2)c1]

The title compound was prepared in analogy to Example 5 using 1-(3-cyano-phenyl)-1H-pyrazole-4-carboxylic acid (CAS 345966-94-1) instead of 1-(3-fluorophenyl)-1H-pyrazole-4-carboxylic acid in step a).

White solid. MS (ISP): 374.2 ([M+H]⁺).

Example 14

(S)—N-(4-(morpholin-2-yl)phenyl)-1-(4-(trifluoromethyl)pyridin-2-yl)-1H-pyrazole-4-carboxamide hydrochloride

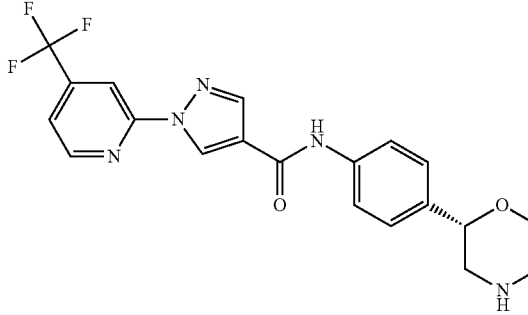

a) (S)-Tert-butyl 2-(4-(1H-pyrazole-4-carboxamido)phenyl)morpholine-4-carboxylate In a 100 mL round-bottomed flask, (S)-tert-butyl 2-(4-aminophenyl)morpholine-4-carboxylate (12.5 g, 44.9 mmol, Eq: 1.00), 1H-pyrazole-4-carboxylic acid (5.03 g, 44.9 mmol, Eq: 1.00), HBTU (25.5 g, 67.4 mmol, Eq: 1.5) and N-methylmorpholine (13.6 g, 14.8 ml, 135 mmol, Eq: 3) were combined with DMF (1250 ml) to give a light yellow solution. The reaction mixture was stirred at room temperature for 3 days. The reaction mixture was poured into 200 mL H$_2$O, extracted with EtOAc (2×) and washed with brine. The combined organic layers were dried over MgSO$_4$ and concentrated in vacuo.

The crude material was purified by silica gel column chromatography leading to 8.8 g off-white solid. MS (ISP): 373.2 ([M+H]$^+$).

b) (S)-tert-butyl 2-(4-(1-(4-(trifluoromethyl)pyridin-2-yl)-1H-pyrazole-4-carboxamido)phenyl)morpholine-4-carboxylate A suspension of (S)-tert-butyl 2-(4-(1H-pyrazole-4-carboxamido)phenyl)morpholine-4-carboxylate (35 mg, 94.0 µmol, Eq: 1.00), 2-bromo-4-(trifluoromethyl)pyridine (21.1 mg, 94.0 µmol, Eq: 1.00), and potassium carbonate (26.0 mg, 188 µmol, Eq: 2) in DMSO (600 µl) was stirred for 4 hours at 120° C. The reaction mixture was cooled down at room temperature, poured into 5 ml water, extracted with EtOAc and the combined organic phases washed with brine, dried over MgSO$_4$ and concentrated in vacuo. The crude material was suspended in heptane/EtOAc, 9:1 and stirred for 1 hour at room temperature. The suspension was filtered off and dried under high vacuum leading to 31 mg white solid. MS (ISP): 518.2 ([M+H]$^+$).

c) (S)—N-(4-(morpholin-2-yl)phenyl)-1-(4-(trifluoromethyl)pyridin-2-yl)-1H-pyrazole-4-carboxamide hydrochloride To a suspension of (S)-tert-butyl 2-(4-(1-(4-(trifluoromethyl)pyridin-2-yl)-1H-pyrazole-4-carboxamido)phenyl)morpholine-4-carboxylate (30 mg, 58.0 µmol, Eq: 1.00) in dioxane (100 µl) was added 4 M HCl in dioxane (217 µl, 870 µmol, Eq: 15). The reaction mixture was stirred at 60° C. for 2 hours. The mixture was diluted with 2 ml dioxane and cooled down to room temperature. The suspension was filtered off, washed with ether and dried under high vacuum, leading to a white solid. MS: 418.2 ([M+H]$^+$).

Example 15

(S)-1-(4-chloropyridin-2-yl)-N-(4-(morpholin-2-yl)phenyl)-1H-pyrazole-4-carboxamide hydrochloride

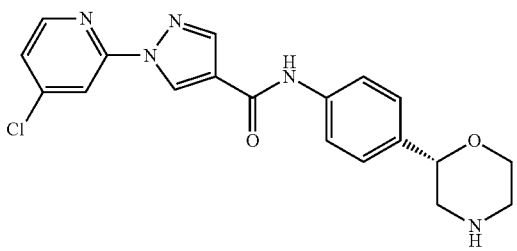 [SMILES: O=C(Nc1ccc([C@H]2CNCCO2)cc1)c1cnn(-c2cc(Cl)ccn2)c1]

The title compound was prepared in analogy to Example 14 using 2-bromo-4-chloropyridine instead of 2-bromo-4-(trifluoromethyl)pyridine in step b).

White solid. MS (ISP): 384.2 ([M+H]$^+$).

Example 16

(S)-1-(2-bromopyridin-4-yl)-N-(4-(morpholin-2-yl)phenyl)-1H-pyrazole-4-carboxamide hydrochloride

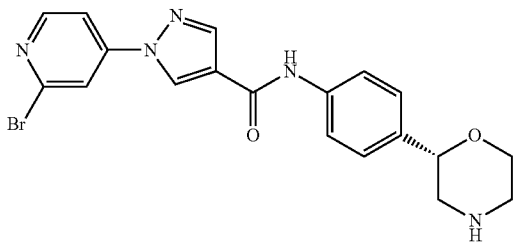

The title compound was prepared in analogy to Example 14 using 2-bromo-4-chloropyridine instead of 2-bromo-4-(trifluoromethyl)pyridine in step b) (side product of Example 15 step b).

White solid. MS (ISP): 428.2 ([M+H]$^+$).

Example 17

(S)-1-(4-bromo-2-cyanophenyl)-N-(4-(morpholin-2-yl)phenyl)-1H-pyrazole-4-carboxamide hydrochloride

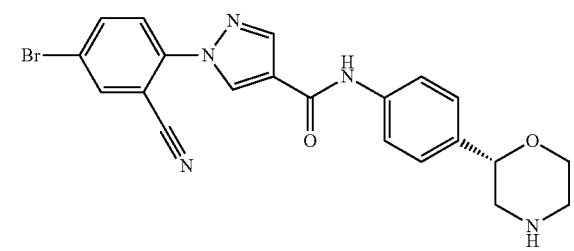 [SMILES: N#Cc1cc(Br)ccc1-n1cc(C(=O)Nc2ccc([C@H]3CNCCO3)cc2)cn1]

The title compound was prepared in analogy to Example 14 using 5-bromo-2-fluorobenzonitrile instead of 2-bromo-4-(trifluoromethyl)pyridine in step b).

Light yellow solid. MS (ISP): 454.1 ([M+H]$^+$).

Example 18

(S)-1-(6-methoxypyridin-2-yl)-N-(4-(morpholin-2-yl)phenyl)-1H-pyrazole-4-carboxamide hydrochloride

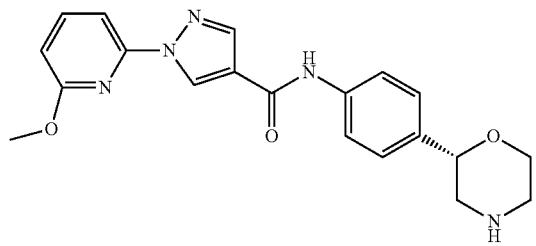 [SMILES: COc1cccc(-n2cc(C(=O)Nc3ccc([C@H]4CNCCO4)cc3)cn2)n1]

a) (S)-tert-butyl 2-(4-(1-(6-methoxypyridin-2-yl)-1H-pyrazole-4-carboxamido)phenyl)morpholine-4-carboxylate Under N$_2$, 1-(6-methoxypyridin-2-yl)-1H-pyrazole-4-carboxylic acid (CAS 1342157-52-1) (0.785 g, 3.58 mmol, Eq: 1.00) was suspended in CH$_2$Cl$_2$ (4.00 ml). 1-chloro-N,N2-trimethypropenylamine (550 mg, 545 µl, 4.12 mmol, Eq: 1.15) was added dropwise. After 15 minutes at RT, the reaction mixture became a brown solution (acid chloride). (S)-Tert-butyl 2-(4-aminophenyl)morpholine-4-carboxylate (997 mg, 3.58 mmol, Eq: 1) was dissolved in CH$_2$Cl$_2$ (4.00 ml) and ethyldiisopropylamine (1.16 g, 1.48 ml, 8.95 mmol, Eq: 2.5) was added. To this solution, the acid chloride solution above was added dropwise and the reaction mixture was stirred at RT over 30 minutes. The reaction mixture was extracted with CH$_2$Cl$_2$ and 1 M citric acid solution; the organic phase was dried over MgSO$_4$; filtered; then concentrated in vacuo. The crude material was purified by flash chromatography (silica gel, 100 g, 5% to 60% EtOAc in heptane) leading to 1.71 g light yellow foam. MS (ISP): 480.1 ([M+H]$^+$).

b) (S)-1-(6-methoxypyridin-2-yl)-N-(4-(morpholin-2-yl)phenyl)-1H-pyrazole-4-carboxamide hydrochloride Under N$_2$, (S)-tert-butyl 2-(4-(1-(6-methoxypyridin-2-yl)-1H-pyrazole-4-carboxamido)phenyl)morpholine-4-carboxylate (1.520 g, 3.17 mmol, Eq: 1.00) was dissolved in dioxane (3 ml). 4 M HCl in dioxane (11.9 ml, 47.5 mmol, Eq: 15) was added dropwise (the reaction mixture became a white suspension). The reaction mixture was stirred at RT over 1 hour. The solvent was evaporated and the residue was dried under high vacuum.

The residue was recrystalisated in 200 ml EtOH (reflux); the solvent was evaporated till 40 ml EtOH was left; the white suspension was filtered, leading to 1.05 g white solid; MS (ISP): 380.2 ([M+H]$^+$).

Example 19

(S)-1-(3-fluoro-5-(trifluoromethyl)pyridin-2-yl)-N-(4-(morpholin-2-yl)phenyl)-1H-pyrazole-4-carboxamide hydrochloride

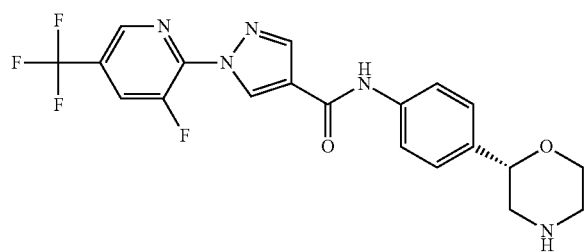 [SMILES: O=C(Nc1ccc([C@H]2CNCCO2)cc1)c1cnn(-c2ncc(C(F)(F)F)cc2F)c1]

The title compound was prepared in analogy to Example 14 using 2-bromo-3-fluoro-5-(trifluoromethyl)pyridine instead of 2-bromo-4-(trifluoromethyl)pyridine and heating for 22 hours instead of 4 hours at 120° C. in step b).

Light yellow solid. MS (ISP): 436.2 ([M+H]$^+$).

Example 20

(S)-1-(2-chloropyridin-4-yl)-N-(4-(morpholin-2-yl)phenyl)-1H-pyrazole-4-carboxamide hydrochloride

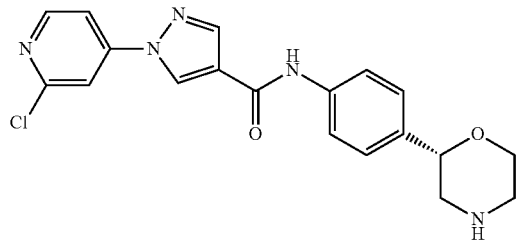 [SMILES: O=C(Nc1ccc([C@H]2CNCCO2)cc1)c1cnn(-c2ccnc(Cl)c2)c1]

The title compound was prepared in analogy to Example 14 using 2-chloro-4-iodopyridine instead of 2-bromo-4-(trifluoromethyl)pyridine and heating for 22 hours instead of 4 hours at 120° C. in step b).

Off-white solid. MS (ISP): 384.2 ([M+H]$^+$).

Example 21

(S)-1-(4-(difluoromethoxy)phenyl)-N-(4-(morpholin-2-yl)phenyl)-1H-pyrazole-4-carboxamide hydrochloride

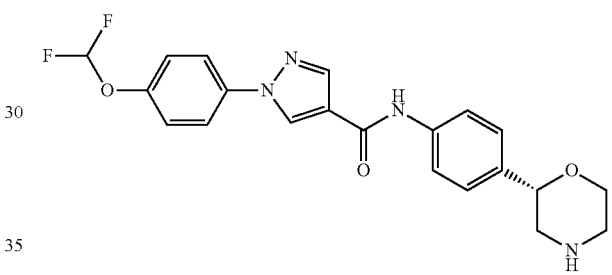

The title compound was prepared in analogy to Example 5 using 1-(4-difluoromethoxy-phenyl)-1H-pyrazole-4-carboxylic acid instead of 1-(3-fluorophenyl)-1H-pyrazole-4-carboxylic acid in step a).

White solid. MS (ISP): 415.3 ([M+H]$^+$).

Preparation of 1-(4-Difluoromethoxy-phenyl)-1H-pyrazole-4-carboxylic acid: see example 26 a-b Example 22

(S)-1-(3-(difluoromethoxy)phenyl)-N-(4-(morpholin-2-yl)phenyl)-1H-pyrazole-4-carboxamide hydrochloride

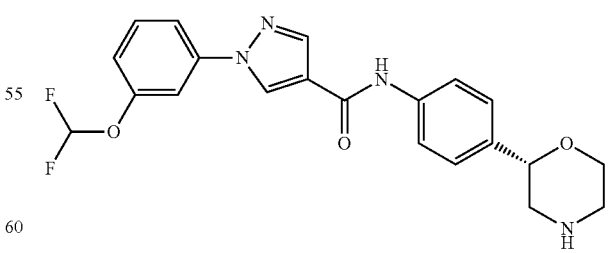

The title compound was prepared in analogy to Example 5 using 1-(3-(difluoromethoxy)phenyl)-1H-pyrazole-4-carboxylic acid instead of 1-(3-fluorophenyl)-1H-pyrazole-4-carboxylic acid in step a).

Light brown solid. MS (ISP): 415.3 ([M+H]$^+$).

Preparation of 1-(3-(difluoromethoxy)phenyl)-1H-pyrazole-4-carboxylic acid a) ethyl 1-(3-(difluoromethoxy)phenyl)-1H-pyrazole-4-carboxylate (3-(difluoromethoxy)phenyl)hydrazine hydrochloride (4.2 g, 19.9 mmol; CAS 479581-64-1) was suspended in ethanol (80 ml) and cooled to 0° C. A solution of ethyl 2-formyl-3-oxopropanoate (2.87 g, 19.9 mmol; CAS 80370-42-9) in ethanol (40 ml) was added, and the reaction was stirred overnight. The solvent was removed under reduced pressure and the residue partitioned between sodium bicarbonate solution and ethyl acetate. The organic layers were combined, dried (MgSO$_4$) and evaporated to yield an orange solid. The solid was suspended in pentane (50 ml) and stirred at 35° C. for 90 min. The suspension was cooled in an ice bath for one hour and the solid was filtered and washed with pentane. After drying 5.12 g (91%) of a yellow solid was obtained MS (ISP): 283.1 ([M+H]$^+$).

b) 1-(3-(difluoromethoxy)phenyl)-1H-pyrazole-4-carboxylic acid

To a solution of ethyl 1-(3-(difluoromethoxy)phenyl)-1H-pyrazole-4-carboxylate (5 g, 17.7 mmol) in a mixture of THF (100 ml), methanol (50 ml) and water (50 ml) lithium hydroxide hydrate (2.23 g, 53.1 mmol) was added. The solution was heated to 80° C. for 2 h. Most of the organic solvent was removed under reduced pressure. Sodium bicarbonate solution was added and the organic layer was separated. The aqueous layer was made acidic by addition of 25% aq. hydrochloric acid (until acidic pH) and the mixture was extracted two times with ethyl acetate. The organic layers were combined, dried (MgSO$_4$) and evaporated to yield a solid.

The solid was stirred in a mixture of heptane and ethyl acetate for 2 h, filtered off and dried to yield 1-(3-(difluoromethoxy)phenyl)-1H-pyrazole-4-carboxylic acid as an off-white solid (3.5 g, 78%).

Example 23

(S)-1-(4-cyano-2-fluorophenyl)-N-(4-(morpholin-2-yl)phenyl)-1H-pyrazole-4-carboxamide hydrochloride

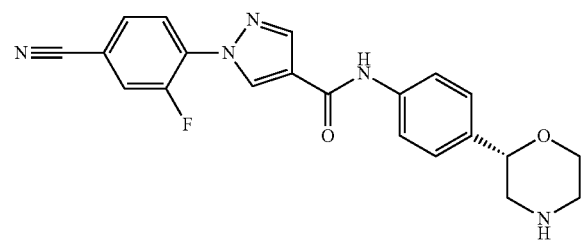

The title compound was prepared in analogy to Example 14 using 3,4-difluorobenzonitrile instead of 2-bromo-4-(trifluoromethyl)pyridine and heating at 120° C. for 24 h in step b).

White solid. MS (ISP): 392.1 ([M+H]$^+$).

Example 24

(S)-1-(4-cyano-3-fluorophenyl)-N-(4-(morpholin-2-yl)phenyl)-1H-pyrazole-4-carboxamide hydrochloride

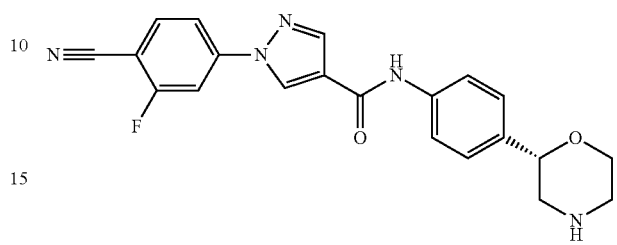

The title compound was prepared in analogy to Example 14 using 2,4-difluorobenzonitrile instead of 2-bromo-4-(trifluoromethyl)pyridine and heating at 120° C. for 24 h in step b).

Yellow solid. MS (ISP): 392.3 ([M+H]$^+$).

Example 25

(S)-1-(2-cyano-4-fluorophenyl)-N-(4-(morpholin-2-yl)phenyl)-1H-pyrazole-4-carboxamide hydrochloride

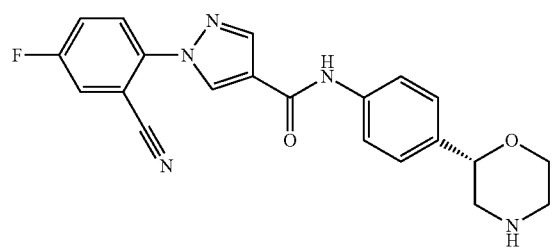 [SMILES: N#Cc1cc(F)ccc1-n1cc(C(=O)Nc2ccc([C@H]3CNCCO3)cc2)cn1]

The title compound was prepared in analogy to Example 14 using 2,4-difluorobenzonitrile instead of 2-bromo-4-(trifluoromethyl)pyridine and heating at 120° C. for 24 h in step b).

Light brown solid. MS (ISP): 392.0 ([M+H]$^+$).

Example 26

(S)—N-(4-(morpholin-2-yl)phenyl)-1-(4-(trifluoromethoxy)phenyl)-1H-pyrazole-4-carboxamide hydrochloride

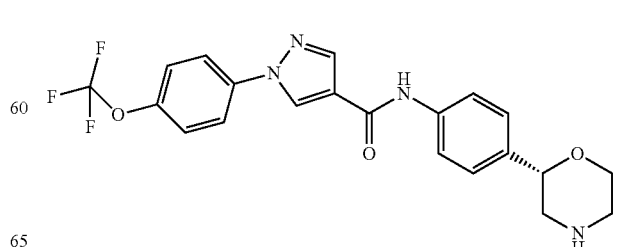

a) ethyl 1-(4-(trifluoromethoxy)phenyl)-1H-pyrazole-4-carboxylate (4-(Trifluoromethoxy)phenyl)hydrazine hydrochloride (229 mg, 1.0 mmol; CAS 133115-72-7) was suspended in ethanol (5 ml) and cooled to 0° C. A solution of ethyl 2-formyl-3-oxopropanoate (2.87 g, 19.9 mmol; CAS 80370-42-9) in ethanol (1 ml) was added, and the reaction was stirred overnight. The solvent was removed under reduced pressure and the residue partitioned between sodium bicarbonate solution and ethyl acetate. The organic layers were combined, dried (MgSO$_4$) and evaporated to yield yellow crystals (241 mg, 80%). The product was used directly for the next step.

b) 1-(3-(difluoromethoxy)phenyl)-1H-pyrazole-4-carboxylic acid

A suspension of ethyl 1-(4-(trifluoromethoxy)phenyl)-1H-pyrazole-4-carboxylate (100 mg, 0.33 mmol) in sodium hydroxide (1.3 ml, 2.66 mmol) was diluted with ethanol (0.2 ml) and shaken at 80° C. for 30 min. After 30 min 0.5 ml ethanol was added and shaking was continued at 90° C. for 1 h. The mixture forms a gel on cooling. 1 ml of water was added and shaking was continued at room temperature overnight. The gel was heated to 80° C., 1 ml of water was added and the mixture was extracted with two times 1 ml of ethyl acetate to remove some starting material. The mixture was acidified with 25% aqueous hydrochloric acid and extracted with ethyl acetate three times. The organic layers were combined, dried (MgSO$_4$) and evaporated to yield an off-white solid (84 mg, 93%) which showed poor solubility in organic solvents.

c) (S)-tert-butyl 2-(4-(1-(4-(trifluoromethoxy)phenyl)-1H-pyrazole-4-carboxamido)phenyl)morpholine-4-carboxylate (S)-tert-Butyl 2-(4-aminophenyl)morpholine-4-carboxylate (60 mg, 0.216 mmol), 1-(4-(trifluoromethoxy)phenyl)-1H-pyrazole-4-carboxylic acid (58 mg, 0.21 mmol), HBTU (123 mg, 0.325 mmol) and N-methylmorpholine (65 mg, 71 µl, 0.65 mmol) were combined with DMF (2.5 ml) to give a light yellow solution. The reaction mixture was stirred at room temperature for 17 hours. The reaction mixture was poured into 25 ml of water and extracted with ethyl acetate twice. The combined organic layers were washed with brine, dried over MgSO$_4$ and concentrated in vacuo. The crude material was purified by flash chromatography (20 g Silicagel, 30 to 50% ethyl acetate in heptane) to yield a white solid (66 mg, 57%). MS (ISP): 477.1 ([M−tBu+H]$^+$), 533.1 ([M+H]$^+$).

d) (S)—N-(4-(morpholin-2-yl)phenyl)-1-(4-(trifluoromethoxy)phenyl)-1H-pyrazole-4-carboxamide hydrochloride (S)-tert-Butyl 2-(4-(1-(4-(trifluoromethoxy)phenyl)-1H-pyrazole-4-carboxamido)phenyl)morpholine-4-carboxylate (60 mg, 0.11 mmol) was dissolved in dioxane (0.5 ml) and a solution of HCl in dioxane (4 M, 0.42 ml, 1.69 mmol) was added. The reaction mixture was stirred for 90 min at 60° C. After cooling ether was added, the solid was filtered off, washed with ether and dried in vacuo at 60° C. to afford (S)—N-(4-(morpholin-2-yl)phenyl)-1-(4-(trifluoromethoxy)phenyl)-1H-pyrazole-4-carboxamide hydrochloride (46 mg, 87%) as a white solid. MS (ISP): 433.2 ([M+H]$^+$).

Example 27

(R)-1-(4-(difluoromethoxy)phenyl)-N-(4-(morpholin-2-yl)phenyl)-1H-pyrazole-4-carboxamide hydrochloride

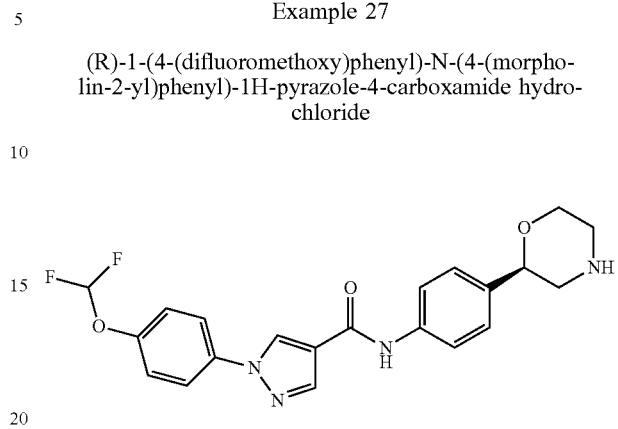

The title compound was obtained in analogy to example 26 using 4-(difluoromethoxy)phenyl)-hydrazine hydrochloride instead of 4-(trifluoromethoxy)phenyl)hydrazine hydrochloride in step a) and (R)-tert-butyl 2-(4-aminophenyl)morpholine-4-carboxylate instead of (S)-tert-butyl 2-(4-aminophenyl)morpholine-4-carboxylate in step c). Off-white solid. MS (ISP): 415.2 ([M+H]$^+$).

Example 28

(S)-1-(6-ethoxypyridin-2-yl)-N-(4-(morpholin-2-yl)phenyl)-1H-pyrazole-4-carboxamide hydrochloride

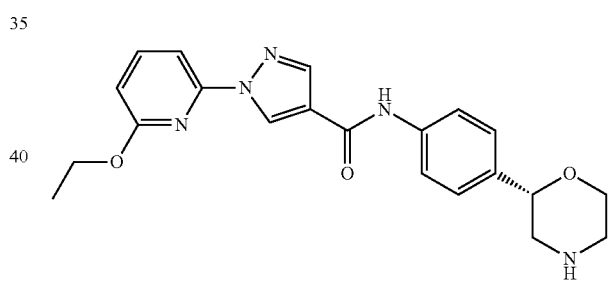

The title compound was prepared in analogy to Example 14 using 2-bromo-6-ethoxypyridine instead of 2-bromo-4-(trifluoromethyl)pyridine and heating at 120° C. for 24 h in step b).

White solid. MS (ISP): 394.1 ([M+H]$^+$).

Example 29

(S)-1-(2,2-difluorobenzo[d][1,3]dioxol-5-yl)-N-(4-(morpholin-2-yl)phenyl)-1H-pyrazole-4-carboxamide hydrochloride

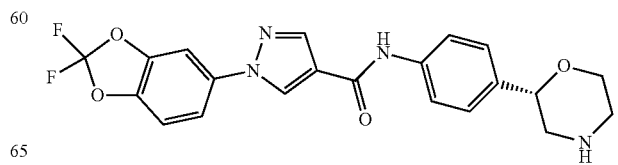

The title compound was obtained in analogy to example 26 using (2,2-difluorobenzo[d][1,3]-dioxol-5-yl)hydrazine hydrochloride instead of 4-(trifluoromethoxy)phenyl)hydrazine hydrochloride in step a). Yellow solid. MS (ISP): 429.3 ([M+H]$^+$).

Example 30

(S)-1-(5-chloropyrimidin-2-yl)-N-(4-(morpholin-2-yl)phenyl)-1H-pyrazole-4-carboxamide hydrochloride

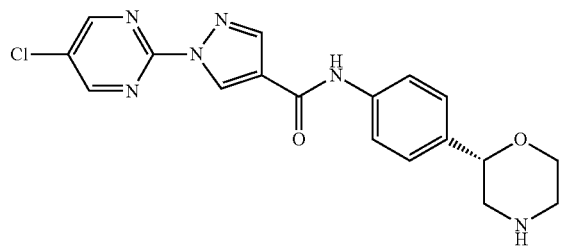

The title compound was prepared in analogy to Example 18 using 1-(5-chloro-pyrimidin-2-yl)-1H-pyrazole-4-carboxylic acid instead of 1-(3-fluorophenyl)-1H-pyrazole-4-carboxylic acid in step a) and heating 30 minutes at 60° C. instead of room temperature in step b).

Off-white solid. MS (ISP): 385.1 ([M+H]$^+$).

Preparation of 1-(5-chloro-pyrimidin-2-yl)-1H-pyrazole-4-carboxylic acid a) ethyl 1-(5-chloropyrimidin-2-yl)-1H-pyrazole-4-carboxylate Under N$_2$, 5-chloro-2-hydrazinylpyrimidine (200 mg, 1.38 mmol, Eq: 1.00) was combined with ethanol (15 ml). 4 M HCl in dioxane (346 µl, 1.38 mmol, Eq: 1.00) (the reaction mixture became a colourless solution) was added and the reaction mixture was cooled to 0° C. (the reaction mixture became a white suspension). A solution of ethyl 2-formyl-3-oxopropanoate (CAS 80370-42-9) (199 mg, 1.38 mmol, Eq: 1.00) in ethanol (2.6 ml) was added (the reaction mixture became a dark yellow suspension), and the reaction was stirred at RT over 1 hour. The solvent was removed and the reaction mixture was suspended in CH$_2$Cl$_2$, filtered-off and concentrated in vacuo to yield 230 mg white solid. MS (ISP): 253.0 ([M+H]$^+$).

b) 1-(5-chloro-pyrimidin-2-yl)-1H-pyrazole-4-carboxylic acid

Under N$_2$, ethyl 1-(5-chloropyrimidin-2-yl)-1H-pyrazole-4-carboxylate (230 mg, 910 µmol, Eq: 1.00) was dissolved in THF (1.5 ml) and water (0.8 ml). 1 M LiOH solution in water (1.18 ml, 1.18 mmol, Eq: 1.3) was added (the reaction mixture became an orange solution) and the reaction mixture was stirred at 80° C. over 2 hours. The solvent was removed under vacuum then diluted in water. The solution was acidified with 1 M HCl solution till pH=2; the acid precipitated; the mixture was filtered and the cake was dried in vacuo, leading to 89 mg off-white solid.

Example 31

(S)-1-(4-(difluoromethoxy)phenyl)-5-methyl-N-(4-(morpholin-2-yl)phenyl)-1H-pyrazole-4-carboxamide hydrochloride

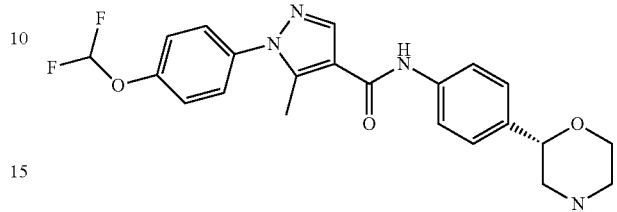

a) tert-butyl 1-(4-(difluoromethoxy)phenyl)-5-methyl-1H-pyrazole-4-carboxylate

Under N$_2$, tert-butyl 3-oxobutanoate (387 mg, 406 µl, 2.37 mmol, Eq: 1.00), p-TsOH mono hydrate (10 mg, 52.6 µmol, Eq: 0.0221) were combined with 1,1-dimethoxy-N,N-dimethylmethanamine (337 mg, 376 µl, 2.66 mmol, Eq: 1.12) in a microwave tube. The yellow solution was heated at 130° C. for 15 min. The resultant dark red solution was concentrated in vacuo and dissolved in acetonitrile (1.8 ml). Triethylamine (1.83 g, 2.5 ml, 18.1 mmol, Eq: 7.61) and (4-(difluoromethoxy)phenyl)hydrazine hydrochloride (0.500 g, 2.37 mmol, Eq: 1.00) were added. The reaction mixture was stirred at RT overnight. The reaction mixture was partitioned between water and EtOAc; extracted; the organic phase was dried over MgSO4; filtered; concentrated in vacuo: 781 mg. The crude material was purified by flash chromatography (silica gel, 70, 5% to 15% EtOAc in heptane).

Yellow solid. MS (ISP): 325.1 ([M+H]$^+$).

In addition, 65 mg tert-butyl 1-(4-(difluoromethoxy)phenyl)-3-methyl-1H-pyrazole-4-carboxylate was isolated as a yellow solid. MS (ISP): 325.1 ([M+H]$^+$).

b) (S)-tert-butyl 2-(4-(1-(4-(difluoromethoxy)phenyl)-5-methyl-1H-pyrazole-4-carboxamido)phenyl)morpholine-4-carboxylate Under N$_2$, tert-butyl 1-(4-(difluoromethoxy)phenyl)-5-methyl-1H-pyrazole-4-carboxylate (0.100 g, 308 µmol, Eq: 1.00) was dissolved in DCM (5.00 ml). Triethylsilane (343 mg, 468 µl, 2.95 mmol, Eq: 9.55) and TFA (696 mg, 468 µl, 6.11 mmol, Eq: 19.8) were added and the reaction mixture was stirred at RT over 4 days. The reagents and solvent were evaporated; dried under high vacuum. The residue was triturated in DCM (3 times) and evaporated. The residue was dissolved in DCM (1.00 ml). 1-Chloro-N,N2-trimethypropenylamine (47.4 mg, 46.9 µl, 355 µmol, Eq: 1.15) was added dropwise. After 10 minutes at RT, a solution containing (S)-tert-butyl 2-(4-aminophenyl)morpholine-4-carboxylate (94.4 mg, 339 µmol, Eq: 1.1) and ethyldiisopropylamine (120 mg, 153 µl, 925 µmol, Eq: 3.00) in DCM (1.00 ml) was added. The reaction mixture was stirred at RT over 30 minutes. The reaction mixture was extracted with CH$_2$Cl$_2$ and 1 M citric acid solution; the organic phase was dried over MgSO$_4$; filtered; concentrated in vacuo. The crude material was purified by flash chromatography (silica gel, 20 g, 5% to 50% EtOAc in heptane) leading to 114 mg of a white solid. EIC: 527.5 (M–H)– c) (S)-1-(4-(difluoromethoxy)phenyl)-5-methyl-N-(4-(morpholin-2-yl)phenyl)-1H-pyrazole-4-carboxamide hydrochloride Under N$_2$, (S)-tert-butyl 2-(4-(1-(4-(difluoromethoxy)phenyl)-5-methyl-1H-pyrazole-4-carboxamido)phenyl)morpholine-4-carboxylate (0.144 g, 272 μmol, Eq: 1.00) was dissolved in dioxane (0.5 ml). 4 M HCl in dioxane (1.02 ml, 4.09 mmol, Eq: 15) was added dropwise (the reaction mixture became a yellow solution). The reaction mixture was stirred at 60° C. over 1 hour. The solvent was evaporated and the residue was dried under high vacuum The residue was triturated in CH$_2$Cl$_2$; filtered and dried under high vacuum, leading to 124 mg white solid. MS (ISP): 429.2 ([M+H]$^+$).

Example 32

(S)-1-(4-(difluoromethoxy)phenyl)-3-methyl-N-(4-(morpholin-2-yl)phenyl)-1H-pyrazole-4-carboxamide hydrochloride

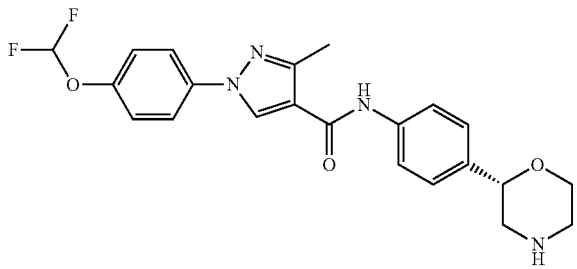 [SMILES: Cc1nn(-c2ccc(OC(F)F)cc2)cc1C(=O)Nc1ccc([C@H]2CNCCO2)cc1]

The title compound was prepared in analogy to Example 31 using tert-butyl 1-(4-(difluoromethoxy)phenyl)-3-methyl-1H-pyrazole-4-carboxylate isolated in step a) in step b).
White solid. MS (ISP): 429.2 ([M+H]$^+$).

Example 33

(S)-1-(6-chloropyrazin-2-yl)-N-(4-(morpholin-2-yl)phenyl)-1H-pyrazole-4-carboxamide hydrochloride

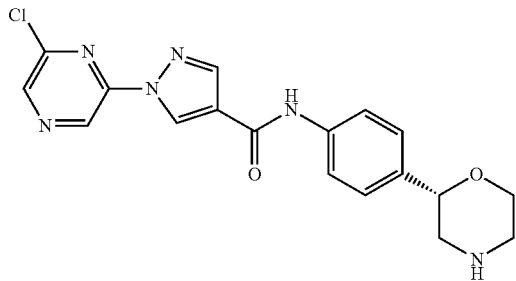 [SMILES: O=C(Nc1ccc([C@H]2CNCCO2)cc1)c1cnn(-c2cncc(Cl)n2)c1]

The title compound was prepared in analogy to Example 18 using 1-(6-chloropyrazin-2-yl)-1H-pyrazole-4-carboxylic acid instead of 1-(6-methoxypyridin-2-yl)-1H-pyrazole-4-carboxylic acid White solid. MS (ISP): 385.1 ([M+H]$^+$).

Preparation of 1-(6-chloropyrazin-2-yl)-1H-pyrazole-4-carboxylic acid: in analogy to 1-(5-chloro-pyrimidin-2-yl)-1H-pyrazole-4-carboxylic acid (Example 30 a-b) using 2-chloro-6-hydrazinylpyrazine hydrochloride instead of 5-chloro-2-hydrazinylpyrimidine in step a).

Example 34

(S)—N-(4-(morpholin-2-yl)phenyl)-1-(2-(trifluoromethyl)pyrimidin-4-yl)-1H-pyrazole-4-carboxamide hydrochloride

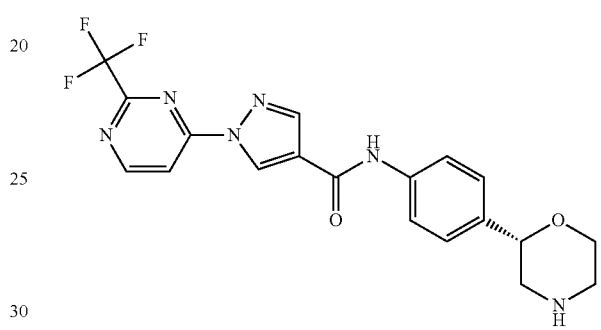

The title compound was prepared in analogy to Example 14 using 4-chloro-2-(trifluoromethyl)pyrimidine instead of 2-bromo-4-(trifluoromethyl) in step b).
White solid. MS (ISP): 419.2 ([M+H]

Example 35

(S)-1-(4-cyanophenyl)-5-methyl-N-(4-(morpholin-2-yl)phenyl)-1H-pyrazole-4-carboxamide hydrochloride

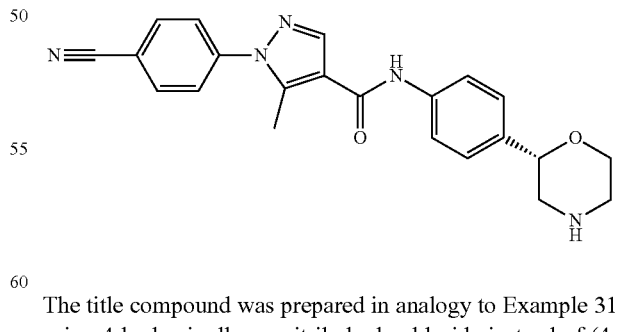

The title compound was prepared in analogy to Example 31 using 4-hydrazinylbenzonitrile hydrochloride instead of (4-(difluoromethoxy)phenyl)hydrazine hydrochloride and methyl 3-oxobutanoate instead of tert-butyl 3-oxobutanoate in step a).

White solid. MS (ISP): 388.4 ([M+H]

Example 36

(S)-1-(2-chloropyrimidin-4-yl)-N-(4-(morpholin-2-yl)phenyl)-1H-pyrazole-4-carboxamide hydrochloride

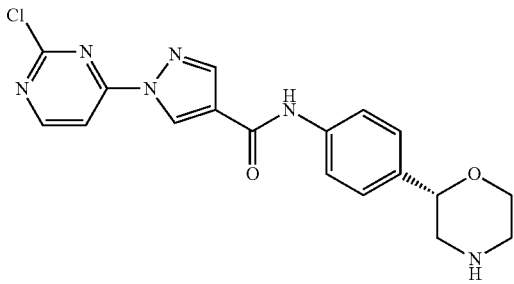 [SMILES: O=C(Nc1ccc([C@H]2CNCCO2)cc1)c1cnn(-c2ccnc(Cl)n2)c1]

The title compound was prepared in analogy to Example 14 using 2,4-dichloropyrimidine instead of 2-bromo-4-(trifluoromethyl)pyridine and 2.5 hours at room temperature in step b).

White solid. MS (ISP): 385.0 ([M+H]

Example 37

(S)—N-(4-(morpholin-2-yl)phenyl)-1-(5-(trifluoromethyl)pyrimidin-2-yl)-1H-pyrazole-4-carboxamide hydrochloride

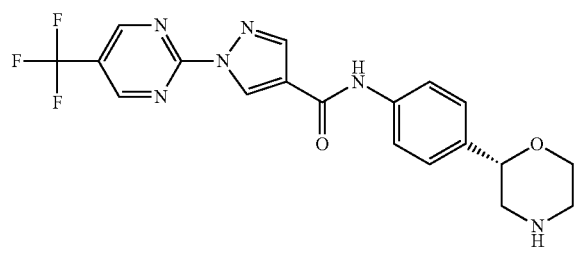 [SMILES: O=C(Nc1ccc([C@H]2CNCCO2)cc1)c1cnn(-c2ncc(C(F)(F)F)cn2)c1]

The title compound was prepared in analogy to Example 14 using 2-chloro-5-(trifluoromethyl)pyrimidine instead of 2-bromo-4-(trifluoromethyl)pyridine and 1 hour at 120° C. in step b).

Off-white solid. MS (ISP): 419.0 ([M+H]+).

Example 38

(S)—N-(4-(morpholin-2-yl)phenyl)-1-(6-(trifluoromethyl)pyrazin-2-yl)-1H-pyrazole-4-carboxamide hydrochloride

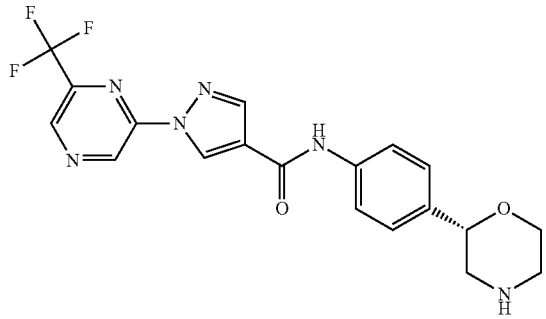 [SMILES: O=C(Nc1ccc([C@H]2CNCCO2)cc1)c1cnn(-c2cncc(C(F)(F)F)n2)c1]

The title compound was prepared in analogy to Example 14 using 2-iodo-6-(trifluoromethyl)pyrazine instead of 2-bromo-4-(trifluoromethyl)pyridine and 1 hour at 120° C. in step b).

Off-white solid. MS (ISP): 419.0 ([M+H]+).

Example 39

(S)-1-(6-methylpyrazin-2-yl)-N-(4-(morpholin-2-yl)phenyl)-1H-pyrazole-4-carboxamide hydrochloride

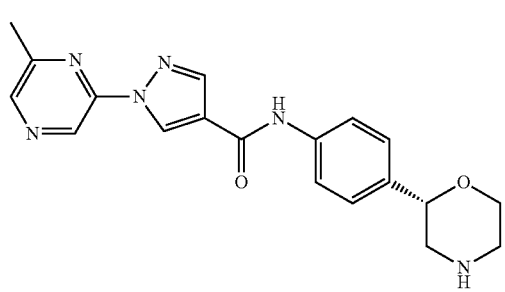 [SMILES: Cc1cncc(-n2cc(C(=O)Nc3ccc([C@H]4CNCCO4)cc3)cn2)n1]

The title compound was prepared in analogy to Example 14 using 2-chloro-6-methylpyrazine instead of 2-bromo-4-(trifluoromethyl)pyridine and 1 hour at 120° C. in step b).

Off-white solid. MS (ISP): 365.2 ([M+H]+).

Example 40

(S)-1-(5-methylpyrazin-2-yl)-N-(4-(morpholin-2-yl)phenyl)-1H-pyrazole-4-carboxamide hydrochloride

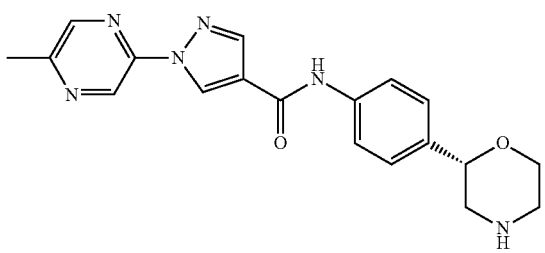 [SMILES: Cc1cnc(-n2cc(C(=O)Nc3ccc([C@H]4CNCCO4)cc3)cn2)cn1]

The title compound was prepared in analogy to Example 14 using 2-chloro-5-methylpyrazine instead of 2-bromo-4-(trifluoromethyl)pyridine and 1 hour at 120° C. in step b).

Off-white solid. MS (ISP): 365.2 ([M+H]+).

Example 41

(S)-1-(3-chloropyrazin-2-yl)-N-(4-(morpholin-2-yl)phenyl)-1H-pyrazole-4-carboxamide hydrochloride

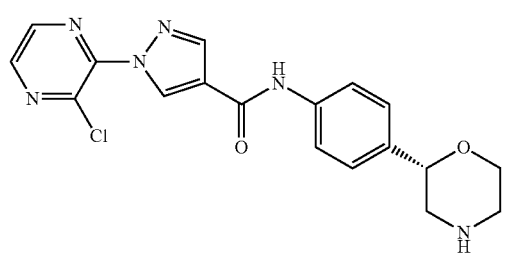 [SMILES: O=C(Nc1ccc([C@H]2CNCCO2)cc1)c1cnn(-c2nccnc2Cl)c1]

The title compound was prepared in analogy to Example 14 using 2,3-dichloropyrazine instead of 2-bromo-4-(trifluoromethyl)pyridine and 1 hour at 120° C. in step b).
White solid. MS (ISP): 385.0 ([M+H]+).

Example 42

(S)-1-(5-cyanopyrazin-2-yl)-N-(4-(morpholin-2-yl)phenyl)-1H-pyrazole-4-carboxamide hydrochloride

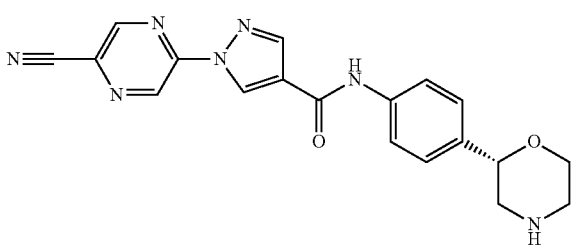 [SMILES: N#Cc1cnc(-n2cc(C(=O)Nc3ccc([C@H]4CNCCO4)cc3)cn2)cn1]

The title compound was prepared in analogy to Example 14 using 5-bromopyrazine-2-carbonitrile instead of 2-bromo-4-(trifluoromethyl)pyridine and 1 hour at 120° C. in step b).
Light yellow solid. MS (ISP): 376.1 ([M+H]+).

Example 43

(S)-1-(4-methylpyrimidin-2-yl)-N-(4-(morpholin-2-yl)phenyl)-1H-pyrazole-4-carboxamide hydrochloride

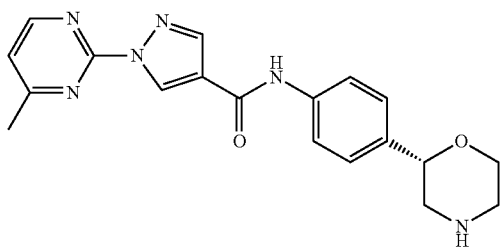 [SMILES: Cc1ccnc(-n2cc(C(=O)Nc3ccc([C@H]4CNCCO4)cc3)cn2)n1]

The title compound was prepared in analogy to Example 14 using 2-bromo-4-methylpyrimidine instead of 2-bromo-4-(trifluoromethyl)pyridine in step b).
Off-white solid. MS (ISP): 365.2 ([M+H]+).

Example 44

(S)—N-(4-(morpholin-2-yl)phenyl)-1-(6-(trifluoromethyl)pyrimidin-4-yl)-1H-pyrazole-4-carboxamide hydrochloride

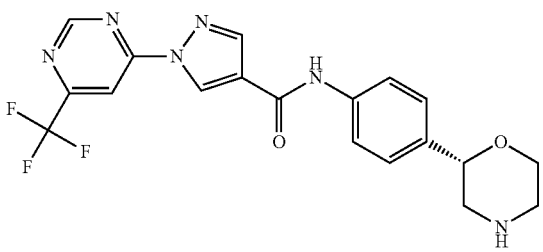 [SMILES: O=C(Nc1ccc([C@H]2CNCCO2)cc1)c1cnn(-c2cc(C(F)(F)F)ncn2)c1]

The title compound was prepared in analogy to Example 14 using 4-chloro-6-(trifluoromethyl)pyrimidine instead of 2-bromo-4-(trifluoromethyl)pyridine in step b).
Off-white solid. MS (ISP): 419.2 ([M+H]+).

Example 45

(S)—N-(4-(morpholin-2-yl)phenyl)-1-(2-(trifluoromethyl)pyrimidin-5-yl)-1H-pyrazole-4-carboxamide hydrochloride

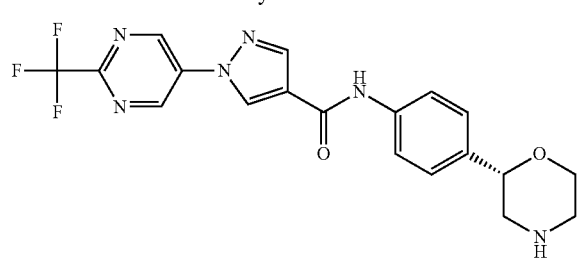

The title compound was prepared in analogy to Example 14 using 5-chloro-2-(trifluoromethyl)pyrimidine instead of 2-bromo-4-(trifluoromethyl)pyridine in step b).
Off-white solid. MS (ISP): 419.2 ([M+H]+).

Example 46

(S)-1-(5-chloropyrazin-2-yl)-N-(4-(morpholin-2-yl)phenyl)-1H-pyrazole-4-carboxamide hydrochloride

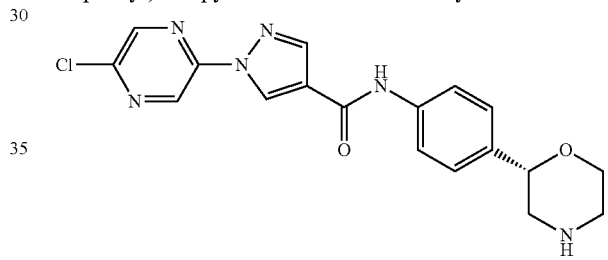

The title compound was prepared in analogy to Example 14 using 2,5-dichloropyrazine instead of 2-bromo-4-(trifluoromethyl)pyridine in step b).
Off-white solid. MS (ISP): 385.0 ([M+H]+).

Example 47

(S)-1-(6-cyanopyrazin-2-yl)-N-(4-(morpholin-2-yl)phenyl)-1H-pyrazole-4-carboxamide hydrochloride

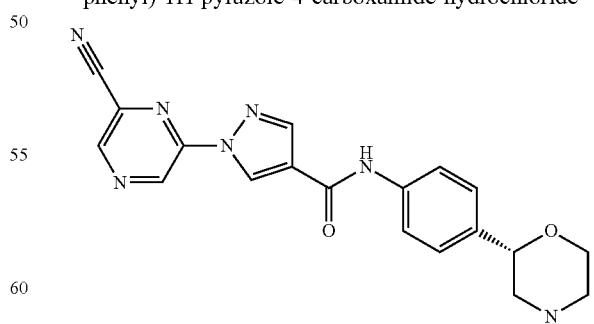

The title compound was prepared in analogy to Example 14 using 6-chloropyrazine-2-carbonitrile instead of 2-bromo-4-(trifluoromethyl)pyridine in step b).
Light yellow solid. MS (ISP): 376.1 ([M+H]+).

Example 48

(S)—N-(4-(morpholin-2-yl)phenyl)-1-(4-(trifluoromethyl)pyrimidin-2-yl)-1H-pyrazole-4-carboxamide hydrochloride

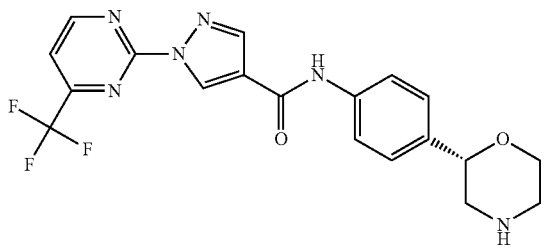 [SMILES: O=C(Nc1ccc([C@H]2CNCCO2)cc1)c1cnn(-c2nccc(C(F)(F)F)n2)c1]

The title compound was prepared in analogy to Example 14 using 2-chloro-4-(trifluoromethyl)pyrimidine instead of 2-bromo-4-(trifluoromethyl)pyridine in step b).
Off-white solid. MS (ISP): 419.2 ([M+H]$^+$).

Example 49

(R)-1-(4-cyano-2-fluorophenyl)-N-(4-(morpholin-2-yl)phenyl)-1H-pyrazole-4-carboxamide hydrochloride

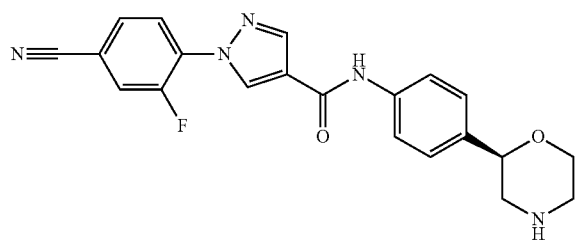 [SMILES: N#Cc1ccc(-n2cc(C(=O)Nc3ccc([C@@H]4CNCCO4)cc3)cn2)c(F)c1]

The title compound was prepared in analogy to Example 14 using 3,4-difluorobenzonitrile instead of 2-bromo-4-(trifluoromethyl)pyridine and (R)-tert-butyl 2-(4-aminophenyl)morpholine-4-carboxylate instead of (S)-tert-butyl 2-(4-aminophenyl)morpholine-4-carboxylate and heating at 120° C. for 24 h in step b).
Light yellow solid. MS (ISP): 392.3 ([M+H]$^+$).

Example 50

(S)—N-(4-(morpholin-2-yl)phenyl)-1-(2-(trifluoromethyl)pyridin-4-yl)-1H-pyrazole-4-carboxamide hydrochloride

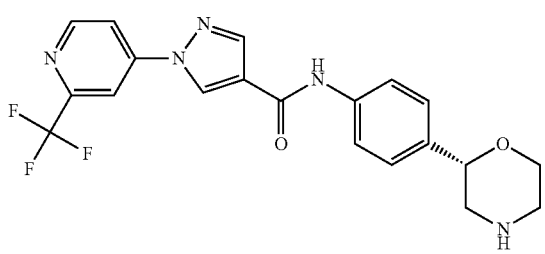 [SMILES: O=C(Nc1ccc([C@H]2CNCCO2)cc1)c1cnn(-c2ccnc(C(F)(F)F)c2)c1]

The title compound was prepared in analogy to Example 14 using 4-chloro-2-(trifluoromethyl)pyridine instead of 2-bromo-4-(trifluoromethyl)pyridine in step b).
White solid. MS (ISP): 418.2 ([M+H]$^+$).

Example 51

(S)—N-(4-(morpholin-2-yl)phenyl)-1-(6-(trifluoromethyl)pyridin-3-yl)-1H-pyrazole-4-carboxamide hydrochloride

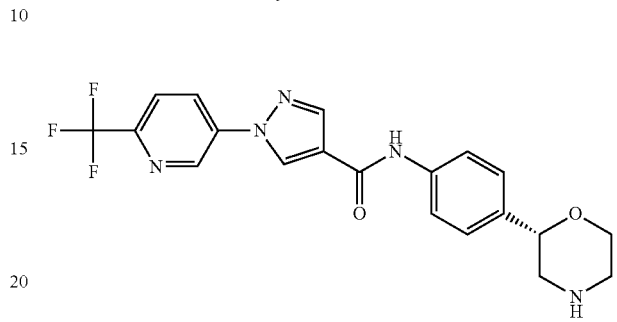

The title compound was prepared in analogy to Example 14 using 5-bromo-2-(trifluoromethyl)pyridine instead of 2-bromo-4-(trifluoromethyl)pyridine in step b).
White solid. MS (ISP): 418.2 ([M+H]$^+$).

Example 52

(S)-1-(3-cyanopyrazin-2-yl)-N-(4-(morpholin-2-yl)phenyl)-1H-pyrazole-4-carboxamide hydrochloride

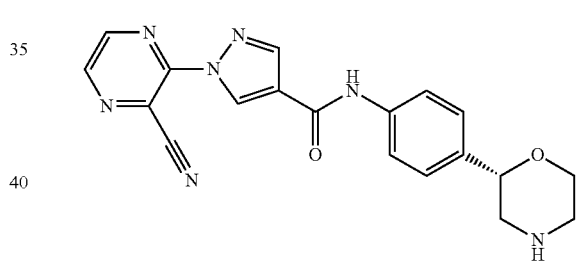

The title compound was prepared in analogy to Example 14 using 3-chloropyrazine-2-carbonitrile instead of 2-bromo-4-(trifluoromethyl)pyridine in step b).
White solid. MS (ISP): 376.4 ([M+H]$^+$).

Example 53

(S)—N-(4-(morpholin-2-yl)phenyl)-1-(5-(trifluoromethyl)pyrazin-2-yl)-1H-pyrazole-4-carboxamide hydrochloride

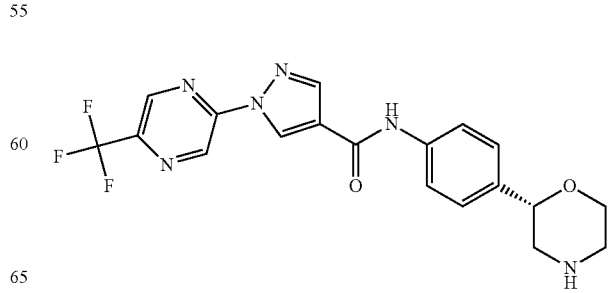

The title compound was prepared in analogy to Example 14 using 2-chloro-5-(trifluoromethyl)pyrazine instead of 2-bromo-4-(trifluoromethyl)pyridine in step b).

Light yellow solid. MS (ISP): 419.9 ([M+H]+).

Example 54

(RS)-1-(4-difluoromethoxy-phenyl)-1H-pyrazole-4-carboxylic acid (4-pyrrolidin-3-yl-phenyl)-amide

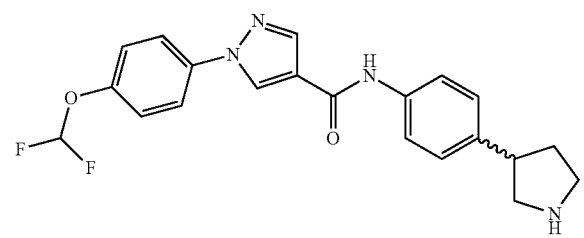 [SMILES: O=C(Nc1ccc(C2CCNC2)cc1)c1cnn(-c2ccc(OC(F)F)cc2)c1]

The title compound was obtained in analogy to example 26 using 4-(difluoromethoxy)phenyl)-hydrazine hydrochloride instead of 4-(trifluoromethoxy)phenyl)hydrazine hydrochloride in step a) and tert-butyl (RS)-3-(4-aminophenyl)pyrrolidine-1-carboxylate instead of (S)-tert-butyl 2-(4-aminophenyl)morpholine-4-carboxylate in step c). White solid. MS (ISP): 399.16 ([M+H]+).

Example 55

(RS)-1-(4-difluoromethoxy-phenyl)-1H-pyrazole-4-carboxylic acid (4-piperidin-3-yl-phenyl)-amide hydrochloride

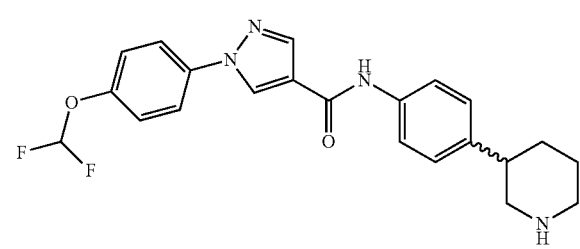 [SMILES: O=C(Nc1ccc(C2CCCNC2)cc1)c1cnn(-c2ccc(OC(F)F)cc2)c1]

The title compound was obtained in analogy to example 26 using 4-(difluoromethoxy)phenyl)-hydrazine hydrochloride instead of 4-(trifluoromethoxy)phenyl)hydrazine hydrochloride in step a) and tert-butyl (RS)-3-(4-aminophenyl)piperidine-1-carboxylate instead of (S)-tert-butyl 2-(4-aminophenyl)morpholine-4-carboxylate in step c). White solid. MS (ISP): 413.6 ([M+H]+).

Example 56

(S)-1-(6-cyclopropylpyrimidin-4-yl)-N-(4-(morpholin-2-yl)phenyl)-1H-pyrazole-4-carboxamide hydrochloride

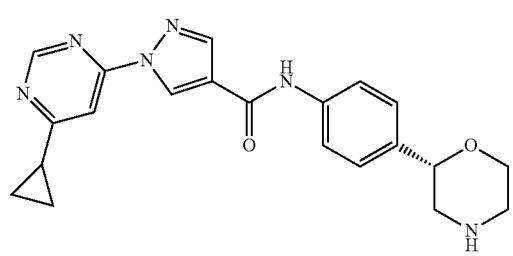 [SMILES: O=C(Nc1ccc([C@H]2CNCCO2)cc1)c1cnn(-c2cc(C3CC3)ncn2)c1]

The title compound was prepared in analogy to Example 14 using 4-chloro-6-cyclopropylpyrimidine instead of 2-bromo-4-(trifluoromethyl)pyridine in step b).

White solid. MS (ISP): 391.6 ([M+H]+).

Example 57

(S)—N-(4-(morpholin-2-yl)phenyl)-1-(4-(trifluoromethyl)thiazol-2-yl)-1H-pyrazole-4-carboxamide hydrochloride

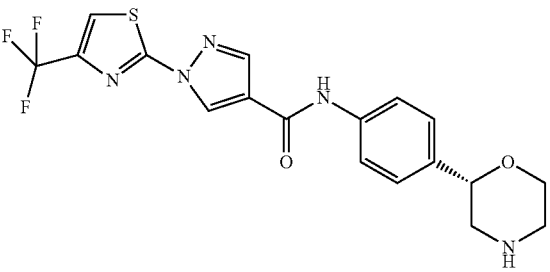 [SMILES: O=C(Nc1ccc([C@H]2CNCCO2)cc1)c1cnn(-c2nc(C(F)(F)F)cs2)c1]

The title compound was prepared in analogy to Example 14 using 2-bromo-4-(trifluoromethyl)thiazole instead of 2-bromo-4-(trifluoromethyl)pyridine in step b).

White solid. MS (ISP): 424.4 ([M+H]+).

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer.

PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1
Membrane Preparation and Radioligand Binding.

HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TrefflLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TrefflLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×Kd in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a $K_i$ value (µM) in mouse or rat on TAAR1 in the range of <0.2 µM as shown in the table below.

| Example | $K_i$ (µM) mouse/rat |
| --- | --- |
| 1 | 0.0086/ 0.229 |
| 2 | 0.0144/ 0.4014 |
| 3 | 0.0025/ 0.0165 |
| 4 | 0.0007/ 0.0033 |

| Example | $K_i$ (μM) mouse/rat |
|---|---|
| 5 | 0.0015/0.0039 |
| 6 | 0.0028/0.007 |
| 7 | 0.0016/0.0046 |
| 8 | 0.0089/0.0147 |
| 9 | 0.0017/0.0043 |
| 10 | 0.0012/0.0041 |
| 11 | 0.0023/0.0023 |
| 12 | 0.0012/0.0011 |
| 13 | 0.0023/0.0072 |
| 14 | 0.0013/0.0019 |
| 15 | 0.0016/0.0036 |
| 16 | 0.0035/0.0029 |
| 17 | 0.0021/0.0015 |
| 18 | 0.001/0.0029 |
| 19 | 0.0135/0.016 |
| 20 | 0.0041/0.0059 |
| 21 | 0.0017/0.004 |
| 22 | 0.001/0.0014 |
| 23 | 0.0041/0.007 |
| 24 | 0.0175/0.0154 |
| 25 | 0.0082/0.0078 |
| 26 | 0.0007/0.0005 |
| 27 | 0.0013/0.001 |
| 28 | 0.0008/0.0022 |
| 29 | 0.0023/0.0014 |
| 30 | 0.0166/0.1352 |
| 31 | 0.0013/0.045 |
| 32 | 0.0008/0.0002 |
| 33 | 0.0032/0.0068 |
| 34 | 0.0054/0.0035 |
| 35 | 0.0601/0.167 |
| 36 | 0.0086/0.0054 |
| 37 | 0.0615/0.0931 |
| 38 | 0.0075/0.0059 |
| 39 | 0.0088/0.0435 |
| 40 | 0.0119/0.1258 |
| 41 | 0.0275/0.0814 |
| 42 | 0.0199/0.0326 |
| 43 | 0.0554/0.315 |
| 44 | 0.0099/0.0041 |
| 45 | 0.0214/0.0059 |
| 46 | 0.0031/0.0056 |
| 47 | 0.0195/0.0345 |
| 48 | 0.0531/0.1486 |
| 49 | 0.0049/0.0033 |
| 50 | 0.0077/0.0038 |
| 51 | 0.0064/0.0048 |
| 52 | 0.0179/0.0451 |
| 53 | 0.0082/0.0038 |
| 54 | 0.0016/0.0011 |
| 55 | 0.002/0.003 |
| 56 | 0.0051/0.0052 |
| 57 | 0.0019/0.0011 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

|      |                          | mg/tablet |       |        |        |
| ---- | ------------------------ | --------- | ----- | ------ | ------ |
| Item | Ingredients              | 5 mg      | 25 mg | 100 mg | 500 mg |
| 1.   | Compound of formula I    | 5         | 25    | 100    | 500    |
| 2.   | Lactose Anhydrous DTG    | 125       | 105   | 30     | 150    |
| 3.   | Sta-Rx 1500              | 6         | 6     | 6      | 30     |
| 4.   | Microcrystalline Cellulose | 30      | 30    | 30     | 150    |
| 5.   | Magnesium Stearate       | 1         | 1     | 1      | 1      |
|      | Total                    | 167       | 167   | 167    | 831    |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|      |                       | mg/capsule |       |        |        |
| ---- | --------------------- | ---------- | ----- | ------ | ------ |
| Item | Ingredients           | 5 mg       | 25 mg | 100 mg | 500 mg |
| 1.   | Compound of formula I | 5          | 25    | 100    | 500    |
| 2.   | Hydrous Lactose       | 159        | 123   | 148    | —      |
| 3.   | Corn Starch           | 25         | 35    | 40     | 70     |
| 4.   | Talc                  | 10         | 15    | 10     | 25     |
| 5.   | Magnesium Stearate    | 1          | 2     | 2      | 5      |
|      | Total                 | 200        | 200   | 300    | 600    |

Manufacturing Procedure

1. Mix items 1, 2 and 3 in a suitable mixer for 30 minutes.
2. Add items 4 and 5 and mix for 3 minutes.
3. Fill into a suitable capsule.

We claim:
1. A compound of formula

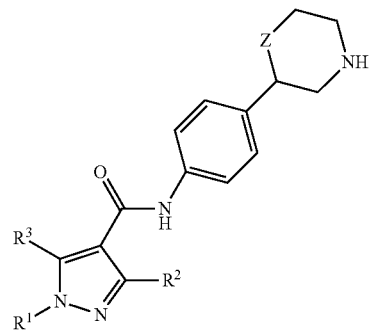

I wherein
$R^1$ is phenyl, optionally substituted by halogen, lower alkyl, lower cycloalkyl, lower alkoxy, cyano, lower alkyl substituted by halogen, lower alkyl substituted by hydroxy, lower alkoxy substituted by halogen or lower alkoxy substituted by hydroxy; or is pyridine-2, 3 or 4-yl, optionally substituted by halogen, lower alkyl, lower cycloalkyl, cyano, lower alkyl substituted by halogen, lower alkyl substituted by hydroxyl, lower alkoxy, lower alkoxy substituted by halogen, or lower alkoxy substituted by hydroxyl; or is
pyrimidin-2, 4 or 5-yl, optionally substituted by halogen, lower alkyl, lower cycloalkyl, lower alkyl substituted by hydroxy or lower alkyl substituted by halogen, or is pyrazin-2-yl, optionally substituted by halogen, lower alkyl, lower cycloalkyl, lower alkyl substituted by halogen, lower alkyl substituted by hydroxy or cyano, or is 2,2-difluorobenzo[d][1,3]dioxol-5-yl, or is
thiazolyl, optionally substituted by lower alkyl substituted by halogen;
$R^2$ is hydrogen or lower alkyl;
$R^3$ is hydrogen, amino or lower alkyl;
Z is a bond, —$CH_2$— or —O—;
or a pharmaceutically suitable acid addition salt thereof.

2. A compound of formula IA according to claim 1,

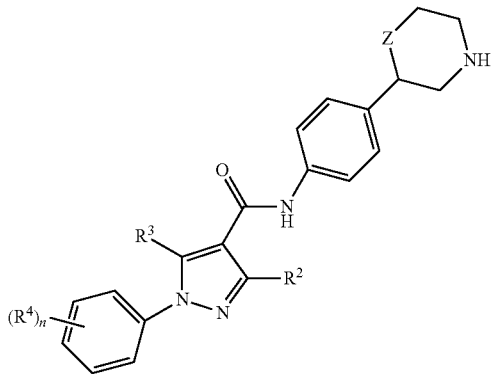

IA wherein
$R^2$ is hydrogen or lower alkyl;
$R^3$ is hydrogen, amino or lower alkyl;

R⁴ is hydrogen, halogen, lower alkyl, lower cycloalkyl, lower alkoxy, cyano, lower alkyl substituted by halogen, lower alkyl substituted by hydroxyl, lower alkoxy substituted by halogen or lower alkoxy substituted by hydroxy;

n is 1 or 2

Z is a bond, —CH$_2$— or —O—;

or a pharmaceutically suitable acid addition salt thereof.

3. A compound according to claim 1, wherein the compounds are (S)-5-methyl-N-(4-(morpholin-2-yl)phenyl)-1-phenyl-1H-pyrazole-4-carboxamide (S)-5-amino-1-(4-fluorophenyl)-N-(4-(morpholin-2-yl)phenyl)-1H-pyrazole-4-carboxamide (S)-1-(4-methoxyphenyl)-N-(4-(morpholin-2-yl)phenyl)-1H-pyrazole-4-carboxamide (S)-1-(4-fluorophenyl)-N-(4-(morpholin-2-yl)phenyl)-1H-pyrazole-4-carboxamide (S)-1-(3-fluorophenyl)-N-(4-(morpholin-2-yl)phenyl)-1H-pyrazole-4-carboxamide (S)-1-(4-cyanophenyl)-N-(4-(morpholin-2-yl)phenyl)-1H-pyrazole-4-carboxamide (R)-1-(4-fluorophenyl)-N-(4-(morpholin-2-yl)phenyl)-1H-pyrazole-4-carboxamide (S)-1-(3-cyanophenyl)-N-(4-(morpholin-2-yl)phenyl)-1H-pyrazole-4-carboxamide (S)-1-(4-bromo-2-cyanophenyl)-N-(4-(morpholin-2-yl)phenyl)-1H-pyrazole-4-carboxamide (S)-1-(4-(difluoromethoxy)phenyl)-N-(4-(morpholin-2-yl)phenyl)-1H-pyrazole-4-carboxamide (S)-1-(3-(difluoromethoxy)phenyl)-N-(4-(morpholin-2-yl)phenyl)-1H-pyrazole-4-carboxamide (S)-1-(4-cyano-2-fluorophenyl)-N-(4-(morpholin-2-yl)phenyl)-1H-pyrazole-4-carboxamide (S)-1-(4-cyano-3-fluorophenyl)-N-(4-(morpholin-2-yl)phenyl)-1H-pyrazole-4-carboxamide (S)-1-(2-cyano-4-fluorophenyl)-N-(4-(morpholin-2-yl)phenyl)-1H-pyrazole-4-carboxamide (S)—N-(4-(morpholin-2-yl)phenyl)-1-(4-(trifluoromethoxy)phenyl)-1H-pyrazole-4-carboxamide (R)-1-(4-(difluoromethoxy)phenyl)-N-(4-(morpholin-2-yl)phenyl)-1H-pyrazole-4-carboxamide (S)-1-(4-(difluoromethoxy)phenyl)-5-methyl-N-(4-(morpholin-2-yl)phenyl)-1H-pyrazole-4-carboxamide (S)-1-(4-(difluoromethoxy)phenyl)-3-methyl-N-(4-(morpholin-2-yl)phenyl)-1H-pyrazole-4-carboxamide (S)-1-(4-cyanophenyl)-5-methyl-N-(4-(morpholin-2-yl)phenyl)-1H-pyrazole-4-carboxamide (R)-1-(4-cyano-2-fluorophenyl)-N-(4-(morpholin-2-yl)phenyl)-1H-pyrazole-4-carboxamide (RS)-1-(4-difluoromethoxy-phenyl)-1H-pyrazole-4-carboxylic acid (4-pyrrolidin-3-yl-phenyl)-amide or (RS)-1-(4-difluoromethoxy-phenyl)-1H-pyrazole-4-carboxylic acid (4-piperidin-3-yl-phenyl)-amide.

4. A compound of formula IB according to claim 1,

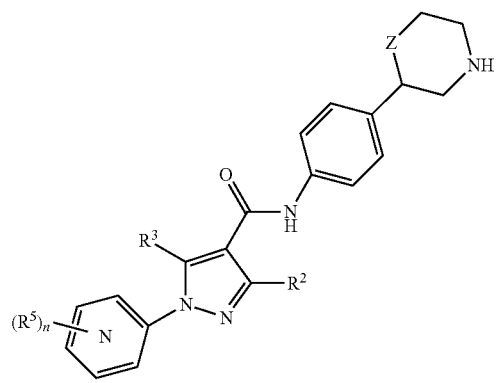

wherein

is pyridine-2, 3 or 4-yl;

R² is hydrogen or lower alkyl;

R³ is hydrogen, amino or lower alkyl;

R⁵ is hydrogen, halogen, lower alkyl, lower cycloalkyl, cyano, lower alkyl substituted by halogen, lower alkyl substituted by hydroxy, lower alkoxy, lower alkoxy substituted by halogen, lower alkoxy substituted by hydroxy;

n is 1 or 2;

Z is a bond, —CH$_2$— or —O—;

or a pharmaceutically suitable acid addition salt thereof.

5. A compound according to claim 1, wherein the compounds are (S)-1-(5-chloropyridin-2-yl)-N-(4-(morpholin-2-yl)phenyl)-1H-pyrazole-4-carboxamide (S)-1-(5-cyanopyridin-2-yl)-N-(4-(morpholin-2-yl)phenyl)-1H-pyrazole-4-carboxamide (S)-1-(5-bromopyridin-2-yl)-N-(4-(morpholin-2-yl)phenyl)-1H-pyrazole-4-carboxamide (S)-1-(5-iodopyridin-2-yl)-N-(4-(morpholin-2-yl)phenyl)-1H-pyrazole-4-carboxamide (S)—N-(4-(morpholin-2-yl)phenyl)-1-(5-(trifluoromethyl)pyridin-2-yl)-1H-pyrazole-4-carboxamide (S)—N-(4-(morpholin-2-yl)phenyl)-1-(4-(trifluoromethyl)pyridin-2-yl)-1H-pyrazole-4-carboxamide (S)-1-(4-chloropyridin-2-yl)-N-(4-(morpholin-2-yl)phenyl)-1H-pyrazole-4-carboxamide (S)-1-(2-bromopyridin-4-yl)-N-(4-(morpholin-2-yl)phenyl)-1H-pyrazole-4-carboxamide (S)-1-(6-methoxypyridin-2-yl)-N-(4-(morpholin-2-yl)phenyl)-1H-pyrazole-4-carboxamide (S)-1-(3-fluoro-5-(trifluoromethyl)pyridin-2-yl)-N-(4-(morpholin-2-yl)phenyl)-1H-pyrazole-4-carboxamide (S)-1-(2-chloropyridin-4-yl)-N-(4-(morpholin-2-yl)phenyl)-1H-pyrazole-4-carboxamide (S)-1-(6-ethoxypyridin-2-yl)-N-(4-(morpholin-2-yl)phenyl)-1H-pyrazole-4-carboxamide (S)—N-(4-(morpholin-2-yl)phenyl)-1-(2-(trifluoromethyl)pyridin-4-yl)-1H-pyrazole-4-carboxamide or (S)—N-(4-(morpholin-2-yl)phenyl)-1-(6-(trifluoromethyl)pyridin-3-yl)-1H-pyrazole-4-carboxamide.

6. A compound of formulas IC1, IC2 and IC3 according to claim 1,

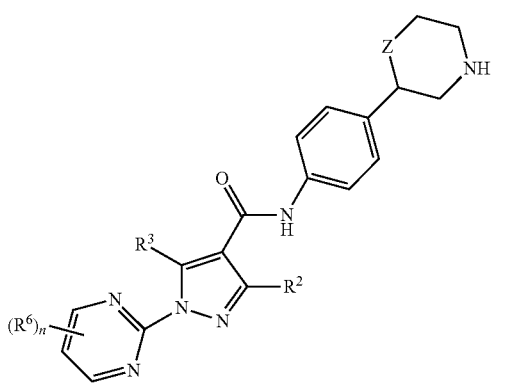

IC1

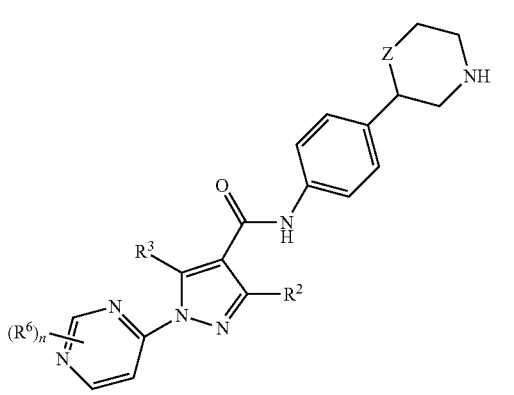

IC2

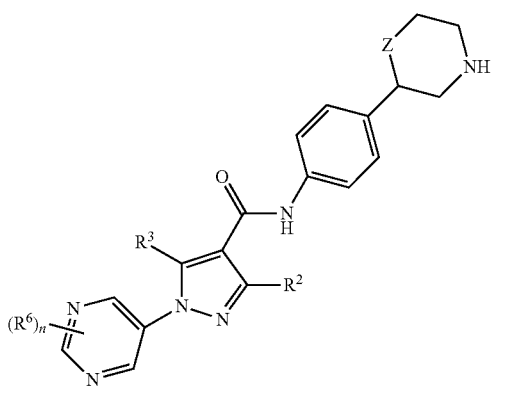

IC3 wherein

R² is hydrogen or lower alkyl;

R³ is hydrogen, amino or lower alkyl;

R⁶ is hydrogen, halogen, lower alkyl, lower cycloalkyl, lower alkyl substituted by halogen or lower alkyl substituted by hydroxy;

Z is a bond, —CH₂— or —O—;

or a pharmaceutically suitable acid addition salt thereof.

7. A compound according to claim 1, wherein the compounds are (S)-1-(5-chloropyrimidin-2-yl)-N-(4-(morpholin-2-yl)phenyl)-1H-pyrazole-4-carboxamide (S)—N-(4-(morpholin-2-yl)phenyl)-1-(2-(trifluoromethyl)pyrimidin-4-yl)-1H-pyrazole-4-carboxamide (S)-1-(2-chloropyrimidin-4-yl)-N-(4-(morpholin-2-yl)phenyl)-1H-pyrazole-4-carboxamide (S)—N-(4-(morpholin-2-yl)phenyl)-1-(5-(trifluoromethyl)pyrimidin-2-yl)-1H-pyrazole-4-carboxamide (S)-1-(4-methylpyrimidin-2-yl)-N-(4-(morpholin-2-yl)phenyl)-1H-pyrazole-4-carboxamide (S)—N-(4-(morpholin-2-yl)phenyl)-1-(6-(trifluoromethyl)pyrimidin-4-yl)-1H-pyrazole-4-carboxamide (S)—N-(4-(morpholin-2-yl)phenyl)-1-(2-(trifluoromethyl)pyrimidin-5-yl)-1H-pyrazole-4-carboxamide (S)—N-(4-(morpholin-2-yl)phenyl)-1-(4-(trifluoromethyl)pyrimidin-2-yl)-1H-pyrazole-4-carboxamide or (S)-1-(6-cyclopropylpyrimidin-4-yl)-N-(4-(morpholin-2-yl)phenyl)-1H-pyrazole-4-carboxamide.

8. A compound of formulas ID according to claim 1,

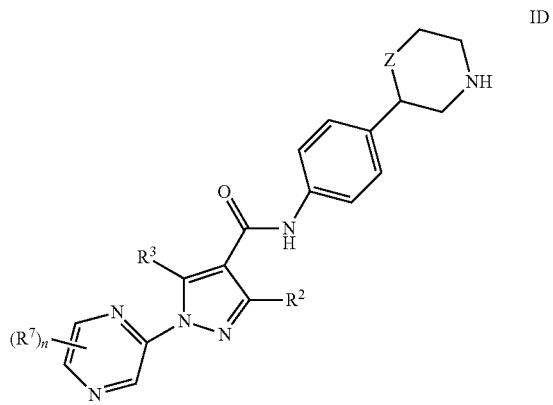

ID wherein

R² is hydrogen or lower alkyl;

R³ is hydrogen, amino or lower alkyl;

R⁷ is hydrogen, halogen, lower alkyl, lower cycloalkyl, lower alkyl substituted by halogen, lower alkyl substituted by hydroxyl or cyano;

Z is a bond, —CH₂— or —O—;

or a pharmaceutically suitable acid addition salt thereof.

9. A compound according to claim 1, wherein the compounds are (S)—N-(4-(morpholin-2-yl)phenyl)-1-(6-(trifluoromethyl)pyrazin-2-yl)-1H-pyrazole-4-carboxamide (S)-1-(6-methylpyrazin-2-yl)-N-(4-(morpholin-2-yl)phenyl)-1H-pyrazole-4-carboxamide (S)-1-(5-methylpyrazin-2-yl)-N-(4-(morpholin-2-yl)phenyl)-1H-pyrazole-4-carboxamide (S)-1-(3-chloropyrazin-2-yl)-N-(4-(morpholin-2-yl)phenyl)-1H-pyrazole-4-carboxamide (S)-1-(5-cyanopyrazin-2-yl)-N-(4-(morpholin-2-yl)phenyl)-1H-pyrazole-4-carboxamide (S)-1-(5-chloropyrazin-2-yl)-N-(4-(morpholin-2-yl)phenyl)-1H-pyrazole-4-carboxamide (S)-1-(6-cyanopyrazin-2-yl)-N-(4-(morpholin-2-yl)phenyl)-1H-pyrazole-4-carboxamide (S)-1-(3-cyanopyrazin-2-yl)-N-(4-(morpholin-2-yl)phenyl)-1H-pyrazole-4-carboxamide or (S)—N-(4-(morpholin-2-yl)phenyl)-1-(5-(trifluoromethyl)pyrazin-2-yl)-1H-pyrazole-4-carboxamide.

10. A compound of formulas IE according to claim 1,

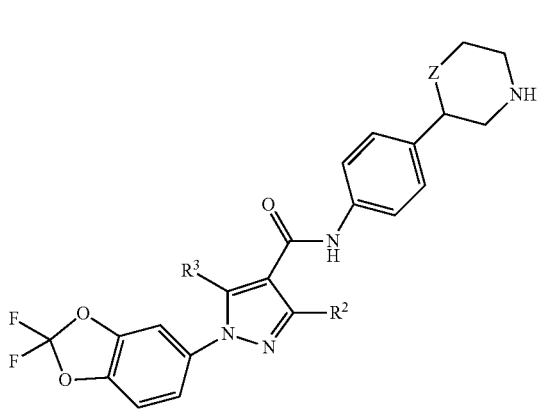

IE wherein
R² is hydrogen or lower alkyl;
R³ is hydrogen, amino or lower alkyl;
Z is a bond, —CH₂— or —O—;
or a pharmaceutically suitable acid addition salt thereof.

11. A compound according to claim 1, wherein the compound is
(S)-1-(2,2-difluorobenzo[d][1,3]dioxol-5-yl)-N-(4-(morpholin-2-yl)phenyl)-1H-pyrazole-4-carboxamide.

12. A compound of formula IF according to claim 1

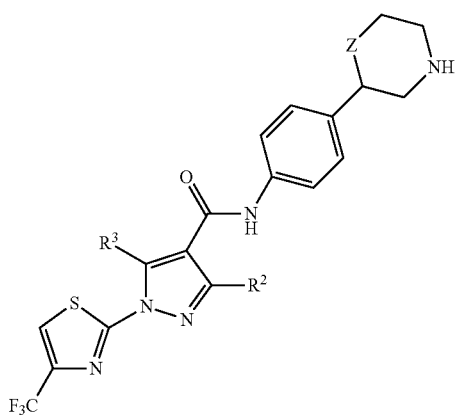

IF wherein
R² is hydrogen or lower alkyl;
R³ is hydrogen, amino or lower alkyl
Z is a bond, —CH₂— or —O—;
or a pharmaceutically suitable acid addition salt thereof.

13. A compound according to claim 1, wherein the compound is
(S)—N-(4-(morpholin-2-yl)phenyl)-1-(4-(trifluoromethyl)thiazol-2-yl)-1H-pyrazole-4-carboxamide.

14. A process for the manufacture of a compound of formula I according to claim 1, which process comprises cleaving off the protecting group of compounds of formula

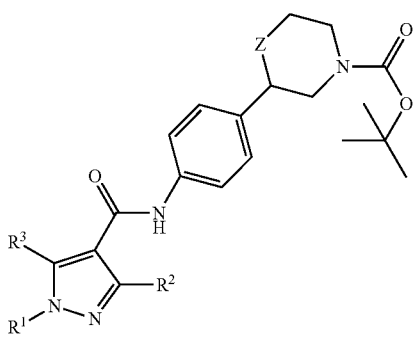

4 to form a compound of formula I

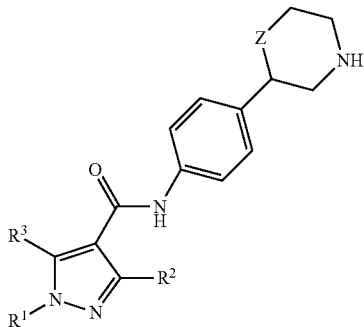

I and, if desired, converting the compounds obtained into pharmaceutically acceptable acid addition salts, wherein the substituents are as described in claim 1.

15. A pharmaceutical composition comprising a compound according to claim 1 and a pharmaceutical acceptable carrier and/or adjuvant.

* * * * *